: US005728943A

United States Patent [19]
Colter, Jr. et al.

[11] Patent Number: 5,728,943
[45] Date of Patent: Mar. 17, 1998

[54] METHOD AND SYSTEM FOR DETECTION AND PREVENTION OF STRESS CORROSION CRACKING IN BURIED STRUCTURES

[75] Inventors: Leslie G. Colter, Jr., Montgomery, Tex.; David C. Katz, Salt Lake City, Utah; Frank E. Rizzo, Spring, Tex.

[73] Assignee: Northwest Pipeline Corporation, Salt Lake City, Utah

[21] Appl. No.: 620,763

[22] Filed: Mar. 15, 1996

[51] Int. Cl.$^6$ .................................................. G01N 17/00
[52] U.S. Cl. ........................................... 73/799; 324/700
[58] Field of Search .............................. 73/799, 865.6, 73/86; 422/53; 204/404; 324/700

[56] References Cited

U.S. PATENT DOCUMENTS

| | | | |
|---|---|---|---|
| 3,770,377 | 11/1973 | Scott et al. | 21/2.7 R |
| 3,846,795 | 11/1974 | Jones | 340/421 |
| 3,973,056 | 8/1976 | Fessler et al. | 427/136 |
| 3,999,121 | 12/1976 | Taylor, Jr. | 422/53 |
| 4,217,180 | 8/1980 | Baxter et al. | 204/1 T |
| 4,282,181 | 8/1981 | Pierce | 422/53 |
| 4,303,885 | 12/1981 | Davis et al. | 324/237 |
| 4,435,984 | 3/1984 | Gruber | 73/628 |
| 4,522,064 | 6/1985 | McMillan | 73/592 |
| 4,560,931 | 12/1985 | Murakami et al. | 324/220 |
| 4,668,303 | 5/1987 | Weber | 134/22.13 |
| 4,685,335 | 8/1987 | Sato et al. | 73/660 |
| 4,794,797 | 1/1989 | Ogawa | 73/786 |
| 4,808,924 | 2/1989 | Cecco et al. | 324/220 |
| 4,808,927 | 2/1989 | Cecco et al. | 324/220 |
| 4,950,552 | 8/1990 | Amend et al. | 428/626 |
| 4,959,177 | 9/1990 | Schutt | 252/391 |
| 5,180,969 | 1/1993 | Kwun et al. | 324/71.2 |
| 5,203,984 | 4/1993 | Sakai et al. | 204/435 |
| 5,227,124 | 7/1993 | Saito et al. | 376/260 |
| 5,307,385 | 4/1994 | Shimanuki et al. | 376/249 |
| 5,351,543 | 10/1994 | Migliori et al. | 73/579 |
| 5,414,353 | 5/1995 | Weischedel | 324/232 |
| 5,461,313 | 10/1995 | Bohon et al. | 324/240 |

FOREIGN PATENT DOCUMENTS 0006139  1/1981  Japan ................................. 73/86

OTHER PUBLICATIONS

"Stress Corrosion Cracking of Carbon Steel in Carbonate Solutions," J.M. Sutcliff, R.R. Fessler, W.K. Boyd and R.N. Parkins. *Corrosion*, vol. 28, No. 8, Aug. 1972, pp. 313–338.

"Technical Note: Stress Corrosion Cracking of X–52 Carbon Steel in Dilute Aqueous Solutions", Z. Szklarska–Smialowska, Z. Xia and R.B. Rebak. *Corrosion*, vol. 50, No. 5, May 1994, pp. 334–338.

"Hydrogen–Induced Stress Corrosion Cracking on a Pipeline", A. Punter, A.T. Fikkers and G. Vanstaen. *Materials Performance*, Jun. 1992, pp. 24–28.

"Modeling Stress–corrosion Cracking of High–Pressure Gas Pipelines", B.N. Leis and R.N. Parkins, Paper No. 19, Source Unknown.

"Major Field Study Compares Pipeline SCC with Coatings", Burke Delanty and John O'Beirne. *Oil and Gas Journal*, Jun. 15, 1992, pp. 39–44.

(List continued on next page.)

*Primary Examiner*—Robert Raevis
*Attorney, Agent, or Firm*—Eleanor V. Goodall

[57] ABSTRACT

A method and system for detecting and preventing Stress Corrosion Cracking (SCC) in buried pipelines or other structures is presented. The basic principle of the invention is to use a plurality of test coupons which are placed in the same environment as a pipeline or other structure of interest as indicators of the development of SCC in the structure of interest. Loading and temperature of the test coupons are controlled. The test coupons are given a range of different Cathodic Protection (CP) levels, with the range of CP levels selected so as to encompass the CP level at which SCC would be expected to occur. The occurrence of cracking in a test coupon indicates levels of CP which will sustain SCC. SCC is prevented in the structure by application of a level of CP which did not sustain SCC.

10 Claims, 21 Drawing Sheets

OTHER PUBLICATIONS

"Transgranular Stress Corrosion Cracking of High–Pressure Pipelines in Contact with Near–Neutral pH Solutions", R.N. Parkins and B.S. Delanty, Paper No. 16, Source Unknown.

"On the Mechanism of Stress Corrosion Cracking of Natural Gas Pipelines", John A. Beavers, Paper No. 17, Source Unknown.

"SCC Threshold Stress in Line Pipe Steels", D.B. Wells, Paper No. 18, Source Unknown.

"Recent Results of Metallurgical Studies on Line–Pipe Steels: Hydrogen–Stress Cracking Behavior", T.P. Groeneveld, Paper No. 20, Source Unknown.

"Factors Affecting the Potential of Galvanostatically Polarized Pipeline Steel in Relation to SCC in $CO_3^{2-}$—$HCO_3^-$ Solutions", R.N. Parkins, C.S. O'Dell and R.R. Fessler, *Corrosion Science*, vol. 24, No. 4, 1984, pp. 343–374.

"Effect of Surface Preparation and Coatings on SCC Susceptibility of Line Pipe: Phase 1—Laboratory Studies", J.A. Beavers, N.G. Thompson and K.E.W. Coulson, Paper No. 597, Paper presented at NACE International's Corrosion 93 Annual Conference.

"Effect of Surface Preparation and Coatings on SCC Susceptibility of Line Pipe: Phase 2—Field Studies", J.A. Beavers, N.G. Thompson and K.E.W. Coulson, Source Unknown, pp. 1–19.

"Electrochemical Processes Controlling SCC of Underground Pipelines", R.B. Rebak, Z. Xia, R. Safruddin and Z. Szklarska–Smialowska, Paper No. 184, Paper presented at NACE International's Corrosion 95 Annual Conference.

"Control of Pipeline Stress Corrosion Cracking is Probed", Wallace E. Almquist, *Oil and Gas Journal*, Oct. 22, 1979, pp. 68–73.

"Stress Corrosion Cracking of Ferritic Steels in $CO_2$—Containing Enviornments", R.N. Parkins, Source Unknown, pp. 45–64.

"Predictive Approaches to Stress Corrosion Cracking", R.N. Parkins, *Corrosion Science*, vol. 20, 1980, pp. 147–166.

"Generation of Stress Corrosion Cracking Environments at Pipeline Surfaces", E.A. Charles and R.N. Parkins, *Corrosion*, vol. 51, No. 7, 1995, pp. 518–527.

The Mechanical Parameters of Stress–Corrosion Cracking, J.C. Scully, *Corrosion Science*, vol. 8, 1968, pp. 759–769.

"On the Propagation of Stress Corrosion Cracks in Metals", J.G. Hines, *Corrosion Science*, vol. 1, 1961, pp. 21–48.

"Strain Rate Effect in Stress Corrosion Cracking", R.N. Parkins, *Corrosion*, vol. 46, No. 3, Mar. 1990, pp. 178–189.

"Stress Corrosion Testing Methods", ASTM, Special Technical Publication 425, pp. 3–20.

"Evaluation of Stress Corrosion Cracking", Donald O. Sprowls, Metals Handbook, pp. 245–282.

"Standard Practice for Preparation and Use of Bent–Beam Stress–Corrosion Test Specimens", ASTM G–39–90, pp. 151–157.

"Standard Practice for Making and Using C–Ring Stress Corrosion Test Specimens", ASTM G38–73, pp. 145–150.

"Test Methods for Low–pH Pipeline SCC: A Comparison of SSRT and Full Scale Testing", W. Zheng, R.W. Revie, F.A. MacLeod, D. Kliff and S. Rajan, Paper No. 187, Paper presented at NACE International's Corrosion 95 Annual Conference.

"A Full–Scale Test Approach to $H_2S$—Induced Environmental Cracking in Large Diameter Saw Pipes: Effects of Forming Processes", C. Bennett, A. Brown, M. Pontremoli, R. Poepperling and A. Streisselberger, Paper 15, Unknown Source.

"Constant Strain Rate Technique for Assessing Stress–Corrosion Susceptibility", J.H. Payer, W.E. Berry and W.K. Boyd, Stress Corrosion—New Approaches, ASTM STP 610, ASTM 1976, pp. 82–93.

"Standard Test Method for Resistivity of Electrical Conductor Materials", ASTM 193–87, pp. 299–302.

"Stress–Concentration Factors for Single Notch in Flat Bar in Pure and Central Bending", M.M. Leven and M.M. Frocht, *Journal of Applied Mechanics*, Dec. 1952, pp. 560–564.

"A Notched Ring Specimen for Hydrogen Embrittlement Studies", F.S. Williams, W. Beck and E.J. Janowsky, Presented at the Sixty–third Annual Meeting of the Society, Jun. 26–Jul. 1, 1960, pp. 1192–1199.

"Stress Analysis of Unnotched C–Rings Used for Stress Cracking Studies", S.O. Fernandez and G.F. Tisinai, *Journal of Engineering for Industry*, Feb. 1968, pp. 147–152.

"Cathodic Protection Levels Under Disbonded Coatings", R.R. Fessler, A.J. Markworth and R.N. Parkins, *Corrosion*, vol. 39, No. 1, Jan. 1983, pp. 20–25.

"A Study of Cathodic Polarization and pH Changes in Metal Crevices", M.H. Peterson and T.J. Lennox, Jr., *Corrosion*, vol. 29, No. 10, Oct. 1973, pp. 406–410.

"Potential and pH Relationships in Cathodically Polarized Metal Crevices", T.J. Lennox, Jr. and M.H. Peterson, Source Unknown, pp. 173–177.

"Low–Cost Electronic Devices for Corrosion Measurements", Robert Baboian and Paul Prew, *Materials Performance*, Jul., 1993, pp. 56–59.

"Field Evaluation of British Gas Wave Inspection System for SCC Detection", C.R. Ward and A.S. Mann, Paper No. 21, Unknown Source.

"Principles and Prevention of Corrosion", D.A. Jones, Macmillan Publishing Company, Chapter 8, pp. 234–242.

"Report on Failure Analysis", M.W. Hukle, Microalloying International Inc., Aug. 4, 1994.

METHOD AND SYSTEM FOR DETECTION AND PREVENTION OF STRESS CORROSION CRACKING IN BURIED STRUCTURES

I. BACKGROUND OF THE INVENTION

A. Field of the Invention

This invention relates to the detection and prevention of stress corrosion cracking (SCC) in buried structures such as pipelines. In particular, it is suitable for the detection and prevention of SCC in low carbon steel structures. SCC is brittle failure which occurs in an alloy at relatively low constant tensile stress in a corrosive environment. SCC has historically been known to be a problem in various structures, including ship hulls, boilers, offshore platforms, cartridge cases, vessels containing coal-gas liquor, etc. More recently it has been realized that low-strength steel structures such as gas pipelines are also subject to SCC.

B. The Background Art

Much of the prior art relating to SCC is directed toward determining the mechanisms underlying SCC. In the case of pipelines, it has been found that pipe failures are typically localized to within five miles of a compressor station, on the downstream side of the compressor(s). Examination of fracture surfaces from the failed sections indicated the occurrence of Intergranular Stress Corrosion Cracking (IGSCC). IGSCC of pipeline steel is generally attributed to the occurrence of a $CO_3^{--}/HCO_3^-$ species in the immediate proximity of the steel's surface. These species are sometimes present in the global environment or generated in an environment due to combination of a coating disbondment, applied cathodic protection (CP), and an abundance of $CO_2$. In the presence of a $CO_3^{--}/HCO_3^-$ environment, carbon steels suffer IGSCC in a narrow range of polarized potentials, typically between −625 and −750 mV vs. a saturated calomel reference electrode (SCE). The critical potential range for $CO_3^{--}/HCO_3^-$ cracking coincides with the formation of an adherent black film believed to be composed of magnetite and iron carbonate. Temperature has an accelerating affect on $CO_3^{--}/HCO_3^-$ cracking in the critical potential range.

Susceptibility to SCC can be detected by an accelerated testing method in which the rate of current decay during reanodization of parts indicates susceptibility to SCC (Baxter et al., U.S. Pat. No. 4,217,180).

Methods of Detecting SCC

Various methods of detecting SCC are known in the prior art. However, these methods are generally not suitable for use in testing pipelines in situ, due to their cost or complexity. At the present, the method most commonly used for testing buried pipelines is hydrostatic testing. This method results in the destruction of portions of pipe which are beginning to show SCC, and as a result necessitates the repair or replacement of portions of pipeline, which is both inconvenient and costly.

Measuring eddy currents in a magnetic field is a method of detecting SCC which can be used in pipelines, tubing, storage tanks, etc. (Bohon et al., U.S. Pat. No. 5,461,313), in "elongated magnetically permeable objects" (Weischedel, U.S. Pat. No. 5,414,353), tanker cargo oil pipes (Murakami et al., U.S. Pat. No. 4,560,931), in tubes (Cecco et al., U.S. Pat. Nos. 4,808,924 and 4,808,927), or other objects (Davis et al., U.S. Pat. No. 4,303,885). The drawbacks of this method are that the system undergoing testing must be taken out of service, and direct contact of test equipment with the system is required. In addition, no provision is made for correcting the damaging conditions.

Another method used to detect SCC is Ultrasound Spectroscopy. In resonant ultrasound spectroscopy, wet and dry objects must be compared to detect cracks (Migliori et al., U.S. Pat. No. 5,351,543). McMillan described the measurement of reflected ultrsound (U.S. Pat. No. 4,552,064). An ultrasonic multiple-beam technique has been proposed for detecting cracks at welds in pipe (Gruber, U.S. Pat. No. 4,435,984). As with the Magnetic Eddy Current method, this method has the drawbacks that the system undergoing testing must be taken out of service, and direct contact of test equipment with the system is required. Furthermore, no provision is made for correcting the damaging conditions.

SCC can also be detected by measuring acoustic emission signals, for example to measure cracks in a rotatable body (Sato et al. U.S. Pat. No. 4,685,335). However, this method is suitable for only certain types of structures, and could not be applied to buried pipelines.

It is also possible to measure the mechanical properties of samples exposed to the same conditions as an item of interest (Shimanuki et al., U.S. Pat. No. 5,307,385; Jones, U.S. Pat. No. 3,846,795). This is the same principle as hydrostatic testing.

Kwun et al. have described a method for measuring harmonics and intermodulation frequencies of electromagnetic waves to detect corrosion in steel reinforcements in concrete (U.S. Pat. No. 5,180,969).

Methods of Preventing SCC

Various methods of preventing SCC are known in the prior art, including impressed current systems, galvanic systems (in which a sacrificial material is used as an anode), applying coatings, and placing inhibitors in the vicinity of the structure. SCC of stainless steel pipe can be prevented by coating the pipe with a metal anodic to stainless steel (Amend et al., U.S. Pat. No. 4,950,552). Placing inhibitors such as calcium monobasic phosphate, sodium monobasic phosphate, sodium tripolyphosphate, potassium silicate into environment of a buried pipeline has been proposed by Fessler et al., (U.S. Pat. No. 3,973,056). Corrosion can be reduced in a liquid medium by adding inhibitors (e.g. amines reacted with carbonyl compounds) to the medium (Scott et al., U.S. Pat. No. 3,770,377). SCC of metal weldments in presence of aqueous alkanol amine solution is reduced by the presence of sulfiding agent (Schutt, U.S. Pat. No. 4,959, 177).

Finally, mechanical approaches can be taken in preventing SCC, such as constructing an internal sleeve to form flushing chamber adjacent to expansion bellows joint (Weber, U.S. Pat. No. 4,668,303), thereby reducing corrosion. This approach could not be easily applied to a pipeline, however.

II. BRIEF SUMMARY AND OBJECTS OF THE INVENTION

The present invention is used to identify cathodic protection (CP) levels at which stress corrosion cracking (SCC) will occur in a buried pipeline, and to provide for the adjustment of CP to a level which will prevent SCC. The invention can be used to detect and prevent SCC in any environment, and successful implementation of the invention is not dependent upon identifying all factors which contribute to SCC. The invention was designed for use with buried low-strength pipelines used to transport gas, but it is not limited thereto, and could be used with other types of structures as well.

The SCC sensor includes multiple coupons placed in the same environment as the structure of interest. In particular, the coupons may be buried in the ground in the vicinity of a pipeline in order to determine the susceptibility of the pipeline to SCC. C-ring coupons are cut from the same type of pipe material as the pipeline. Each C-ring is notched and mechanically loaded to produce stresses higher than those occurring during normal operation of the pipeline. The temperature of the pipeline is monitored, and a temperature-control circuit is used to maintain each coupon at the same temperature as the pipeline. Each coupon is given a different level of CP. The development of cracks due to stress corrosion is detected as a change in the resistance of the coupon. The body of the coupon has a relatively low resistance, and thus the notched region of the coupon, which is subject to SCC, has a high resistance which increases as the crack develops. Once it is determined which level of CP is most effective for preventing SCC in the coupons, that level of CP is applied to the pipeline.

The invention is used to test and correct CP levels at one or more sites along a buried pipeline. It is typically desirable to use the invention to test and correct the CP levels at each type of environment in which the pipeline is buried. Locations at which SCC is most likely to occur (e.g. just downstream of a pumping station) are generally selected as test sites. In practice, the actual number of test sites may be selected on the basis of access to sites (e.g. on private property), and funds available as well as on the different environmental conditions. The invention is not limited to a particular number of test sites.

The primary objectives of the present invention are:

1) to provide a system for detecting and preventing SCC in any environment. This is accomplished by installing the test system in situ. The advantage of this approach is that SCC can be detected and prevented even if all factors which contribute to SCC have not been identified.

2) to prevent SCC without repairing or replacing at-risk structures. This is accomplished by correcting the conditions which lead to SCC in situ, by adjusting the level of CP on the structure. This approach has the advantage of saving both time and money in comparison to repairing and replacing at risk structures.

3) to provide a simple method for detecting and preventing SCC in the field. This is achieved by using a simple resistance measurement technique to detect cracking. It is easier and less expensive to use than other prior art techniques.

4) to detect and prevent SCC in low-carbon steels. This meets the need for detecting and preventing SCC in low-carbon steel structures such as gas pipelines.

III. BRIEF DESCRIPTION OF THE DRAWINGS

IV. DETAILED DESCRIPTION OF THE PREFERRED EMBODIMENT

Figure 1:
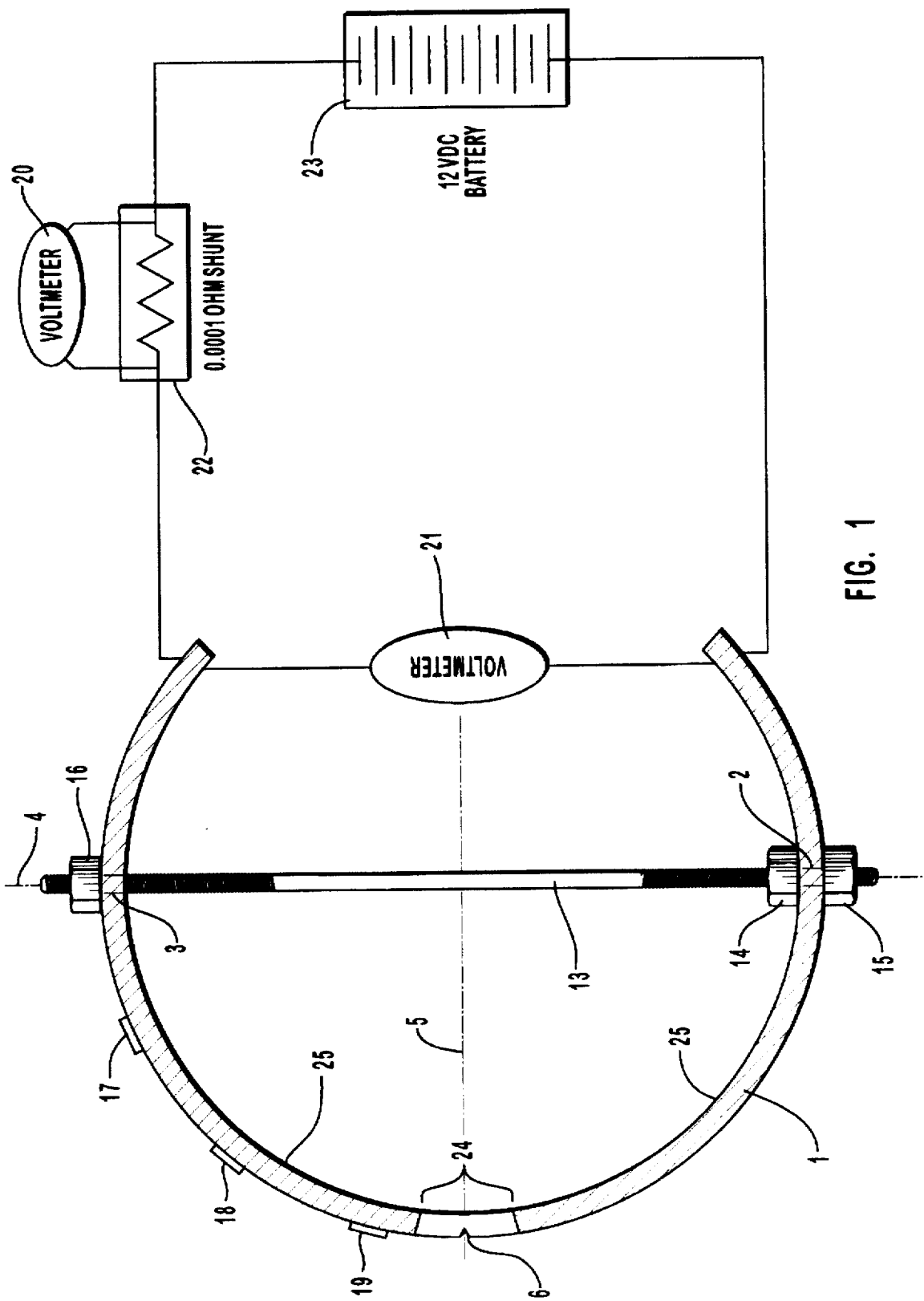
FIG. 1 is a schematic diagram showing the application and monitoring of stress on a test coupon.

The present invention is intended for detection and prevention of SCC in the field, in buried pipelines, or in pipelines, tanks or other structures in other environments. The basic principle of the invention is to use test coupons which are placed in the same environment and maintained at the same temperature as a pipeline or other structure of interest as indicators of the development of SCC in the structure of interest. The test coupons are subjected to a load which is as large or larger than the maximum load which would be experienced by the structure of interest. The test coupons are given a range of different CP levels, with the range of CP levels selected so as to encompass the CP level at which SCC would be expected to occur. Once the level of CP at which SCC occurs (if it does occur) has been identified, the level of CP on the structure of interest is adjusted to a level at which SCC will not occur.

Lab tests were performed during the development of the presently preferred embodiment of the invention. The objectives of the lab tests were to identify the range of polarization potentials at which SCC is likely to occur, to determine the influence of certain parameters on the development of SCC, and to test proper equipment operation. During the lab tests, control variables are set to levels which render the test conditions potent for cracking. The lab tests are described subsequently as Example 1. Example 1 provides detail on the inventive method and also illustrates how the inventive method may be implemented in structures and environments other than buried pipelines. Example 2 describes the design and operation of the presently preferred embodiment of the invention for use in the field, to detect and prevent SCC in buried pipelines.

Example 1

Laboratory Testing

Test Material

The test material used in the laboratory tests was X-52 grade carbon steel. Coupons were cut out of recovered pipeline sections which were removed in conjunction with repairs on a pipeline installed in the field. The alloy element composition of X-52 grade line pipe material is presented below:

| Element | Percentage by Weight (Sample) | Percentage by Weight (Specified Maximum) |
|---|---|---|
| Carbon | 0.29 | 0.34 |
| Manganese | 1.07 | 1.45 |
| Phosphorus | 0.04 | 0.05 |
| Sulfur | 0.03 | 0.06 |
| Silicon | 0.04 | Not Specified |

Mechanical testing was performed on materials removed from service. The results are presented below:

| Property | Test Material | Grade X-52 Min Values |
|---|---|---|
| Tensile Strength | 71,000 psi | 52,000 psi |
| Yield Strength | 92,800 psi | 66,000 psi |
| % Elongation | 24.0% | 22.5% |

Also shown are the minimum acceptable values for any X-52 grade steel for comparative purposes.

Test Coupon

If the system being tested for SCC is a buried pipeline, a C-ring specimen cut from an in-service pipeline section under hoop stress best represents the field loading conditions. A V-notch in the maximum stress area of the C-ring coupon favors crack nucleation, thus controlling the region in which cracking occurs, and accelerates specimen failure. Test coupons were prepared using the American Society for Testing & Materials (ASTM) Standard Practice for Making and Using C-Ring Stress-Corrosion Test Specimens (G38-73). If the system to be tested is something other than a pipeline, another type of test-coupon may be used. ASTM standards for corrosion tests have been established for various types of objects and the selection of an appropriate test coupon is within the ability of a person of ordinary skill in the art.

A schematic of the test coupon setup is shown in FIG. 1. During both lab and field tests, multiple coupons are used, each at a different level of protection. The setup for each coupon is the same, so only a single coupon and its associated equipment is shown in FIG. 1. In this example, a circular ring, 2" wide, was cut out of a 16.5" OD pipe. Water jet machining technique was employed to reduce the buildup of additional stresses within the material or to prevent alteration of material's physical properties immediately adjacent to the cut. Coupon 1 had two 9/16" diameter holes 2 and 3 drilled along a line 4 equivalent to the diameter of the ring. A small section of the ring representing approximately 16.67 percent of the coupon's overall circumference was also removed by water jet machining. The removed section lay equally spaced about a line 5 drawn perpendicular to the line used to fix the 9/16" holes described above. A V-notch 6 with a 60 degree mouth angle and approximately 0.0875 inch depth was then machined in the coupon's outer skin using wire electric discharge machining technique. The notch is located at a point perpendicular to the line 4 and opposite to the side which had the small segment removed. Three 3/16" holes were drilled into each end of the coupon to permit other electrical connections during testing.

Coupon 1 was cleaned using diluted dishwashing detergent to remove grease from the machining process. Next, it was hand polished using increasingly finer grit Silicon-Carbide (Si-C) papers up to 400 grit. Then, the coupon was etched in dilute hydrochloric acid (HCl) to remove surface oxides. Finally, the coupon was rinsed in tap water and air dried.

Several loading arrangements are available for performing SCC testing. The selection of a suitable laboratory loading arrangement was based on the following requirements:

The loading arrangement should be representative of that experienced by a pipeline under pressure and the loading arrangement should favor localization of cracks in the area of maximum stress in order to promote failure in a reasonable time period. Applicable ASTM standards were reviewed in order to select a suitable loading configuration based on the above guidelines. Similarly, an ASTM standard loading configuration for a structure other than a pipeline can be selected by the practitioner of ordinary skill in the art.

A 0.5" fiber glass all-thread rod 13 was positioned through the 9/16" holes 2 and 3 drilled in coupon 1. Two fiberglass nuts 14 and 15 were tightened on either side of hole 2. This procedure fixed one end of coupon 1 to the fiberglass rod 13. A third fiberglass nut 16 was then threaded onto the opposite end of the rod until contact was made with the outer surface of the coupon at hole 3. In this configuration, the continuation of nut 16 down the threaded rod 13 would apply the necessary load or stress upon coupon 1. Three strain gauges 17, 18, 19 were mounted on the external surface of the coupon to quantify the applied load. These were located at 25°, 50°, and 75°, respectively, relative to fiberglass rod 13 which represents the applied stress axis. As nut 16 is tightened against coupon 1, deflection occurs due to the opposite end being anchored. Using an external power supply, a resistor network, a precision voltmeter, and the attached strain gauges, the revolutions of the nut were translated to applied stress. For the purpose of these tests, strain was induced until a stress level of 52,000 psi at the root of the machined notch was obtained. This value equates to 100% of yield strength for X-52 steel. It was found that after 22 complete turns of the loading nut, plastic deformation was achieved, and a decrease in strain was obtained.

Figure 2:
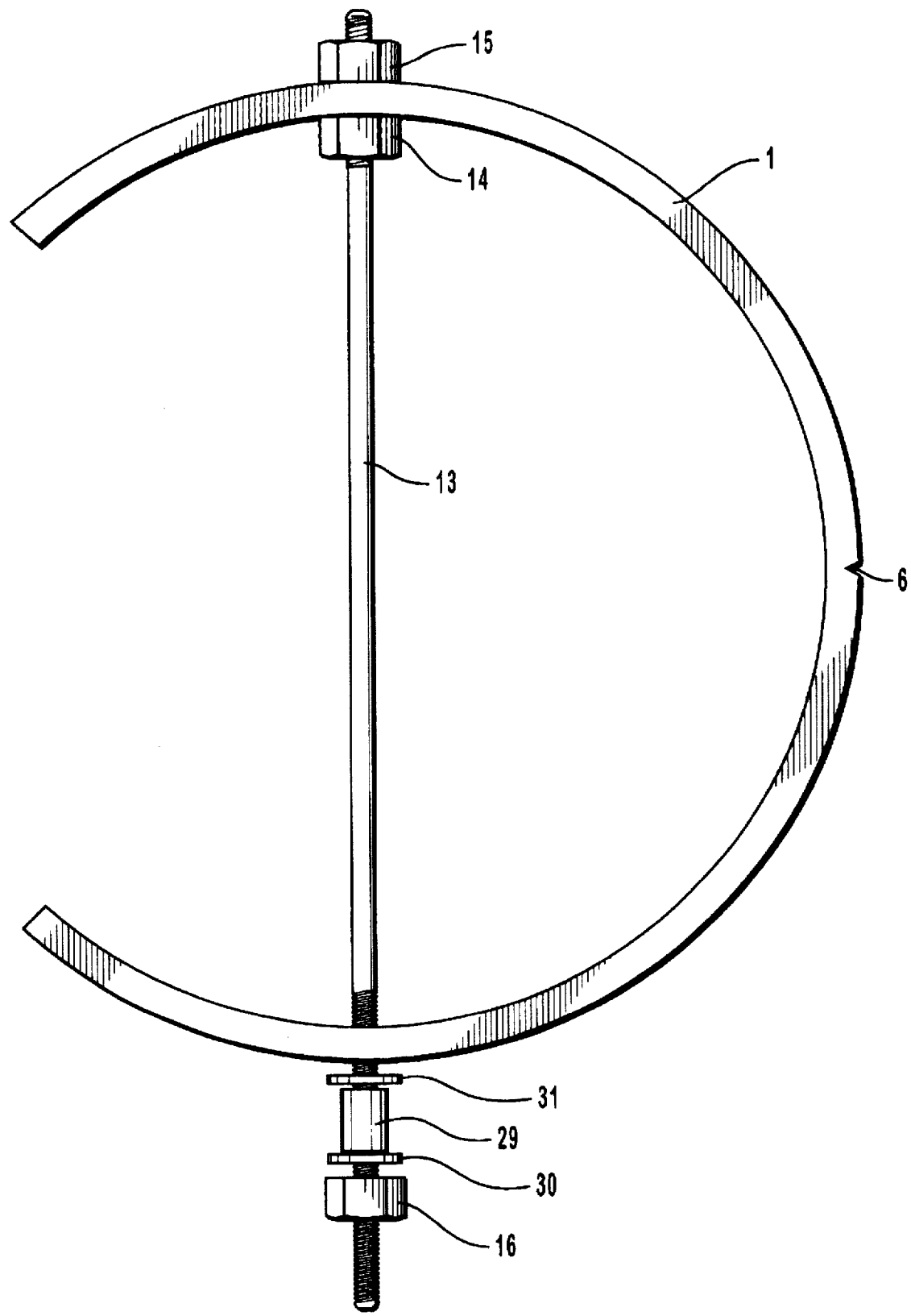
FIG. 2 is a schematic diagram showing an alternative method for applying stress to a test coupon.

As shown in FIG. 2, by adding a helical compression spring 29 (surrounded by washers 30 and 31) between nut 16 and coupon 1, a constant load arrangement was achieved. This was used to maintain a constant stress even after the coupon had begun to deform. This loading arrangement is used in the preferred embodiment of the invention, for both lab and field tests.

Except for a central region 24, which has a total area of about 2"×2" on the convex and concave side of the coupon and the side wall areas, the specimen was covered with heat shrinkable rubber tubing 25. This heat shrinkable rubber tubing protected the remainder of the coupon surface from corrosion effects, so that corrosion was localized at the maximum stress area. At this point, the coupon preparation was complete. A total of six coupons were simultaneously tested during the laboratory experiment.

A voltage-divider circuit comprising a shunt resistor 22 and coupon 1 was used to measure the resistance of the coupon 1. The first end of shunt resistor 22 was connected to the first terminal of current source 23 (which in this example is a 12 Volt battery, but which could be any other suitable current source) and the second end of shunt resistor 22 was connected to the first end of coupon 1. The second end of coupon 1 is connected to the second terminal of current source 23. A first voltage measuring device 20 (which could be a volt meter or other voltage measuring device such as a computer equiped with an analog-to-digital converter) is used to measure the voltage drop across shunt resistor 22. A second voltage measuring device 21 is used to measure the voltage drop across coupon 1.

Test Equipment

Figure 3:
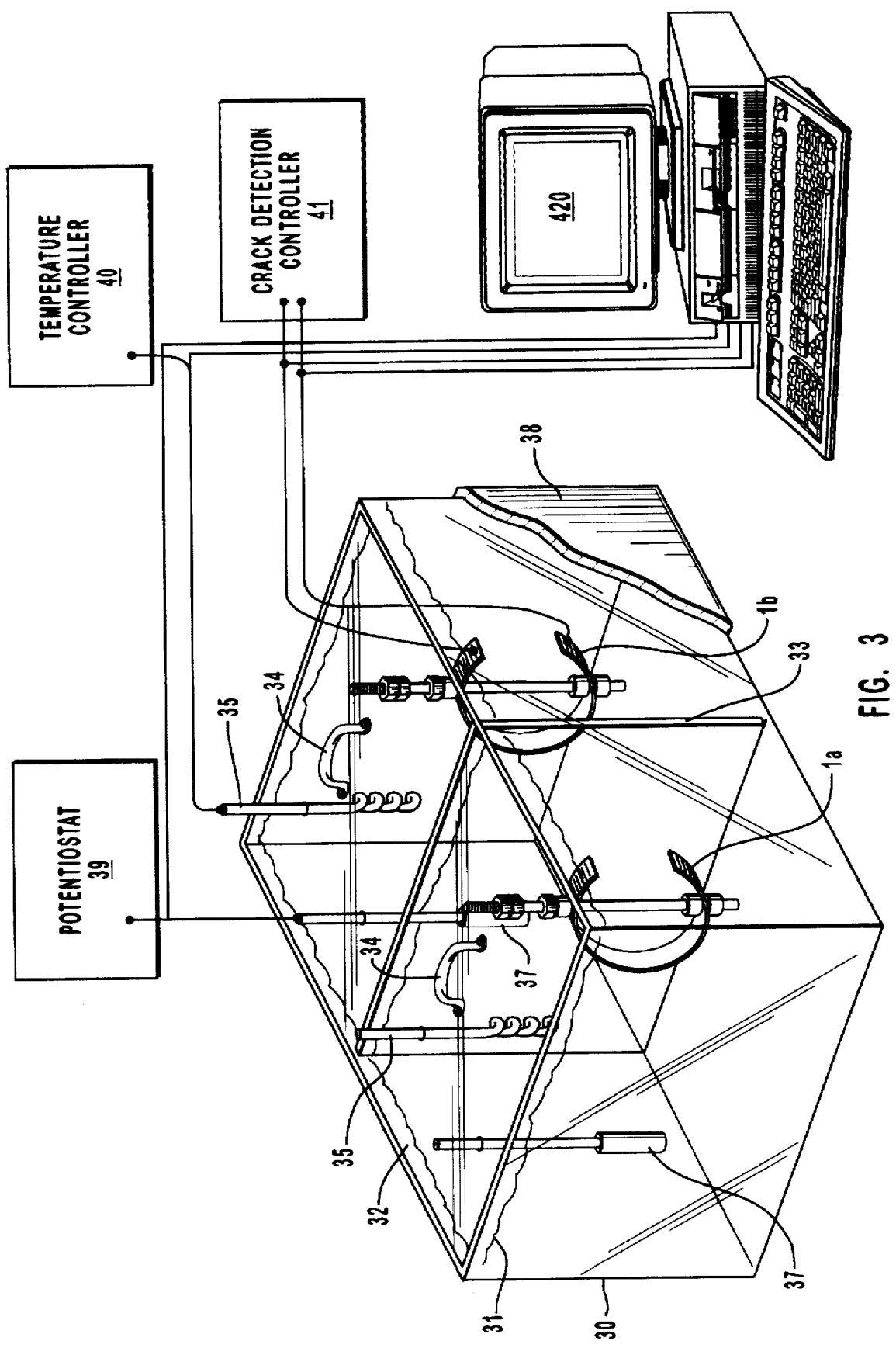
FIG. 3 is an illustration of the embodiment of the invention used in laboratory testing.

Three commercially available aquariums or tropical fish tanks were used as test cells in this work. As shown in FIG. 3, each tank 30 held approximately 25 gallons of prepared electrolyte 31. A custom fiberglass tank cover 32 with an epoxied central separator 33 was used to compartmentalize each of the tanks. The heater side of the tank was separated from the coupon side using a glued Lexan™ sheet. This was to prevent dissolution of copper sheathing surrounding the components found in the immersion heater in subsequent plating of the copper on the exposed section of the coupons. This would halt the growth of any crack because of the passive nature of copper at the potential of the coupon. All of the attachments in each cell were made to these covers. Two cupboard handles 34 were attached to the top cover 32 of the tank to facilitate its easy removal. Provisions were made on each cover to support two test coupons 1a and 1b, two immersion heaters 35, two salt bridges 36 and two auxiliary electrodes 37. The fiberglass separator 33 isolated one of each on either side. Provisions were also made to allow additional electrolyte 31 to be added as necessary to compensate for evaporative loss. The tanks were thermally insulated using CELOTEX$^R$ 38 to minimize heat loss. Potentiostat 39 was used to control the CP level on coupon 1b. An additional potentiostat (not shown) was used to control the CP level on coupon 1a.

Immersion heater 35 was an OGDEN immersion heater, Model KF-1T1-0019-M1. These 0.5 kilowatt heaters had a copper sheath material. Each heater was thermostatically controlled to maintain desired temperature. Temperature controller 40 was used for coupon 1b. The temperature controller for coupon 1a is not shown. Alternatively, any comparable heater could be used to heat the electrolyte, and the invention is not limited by the type of heater used. Crack Detection Controller 41 for coupon 1b, as well as data acquisition computer 42 are also shown in FIG. 3.

Cathodic Protection

Figure 4:
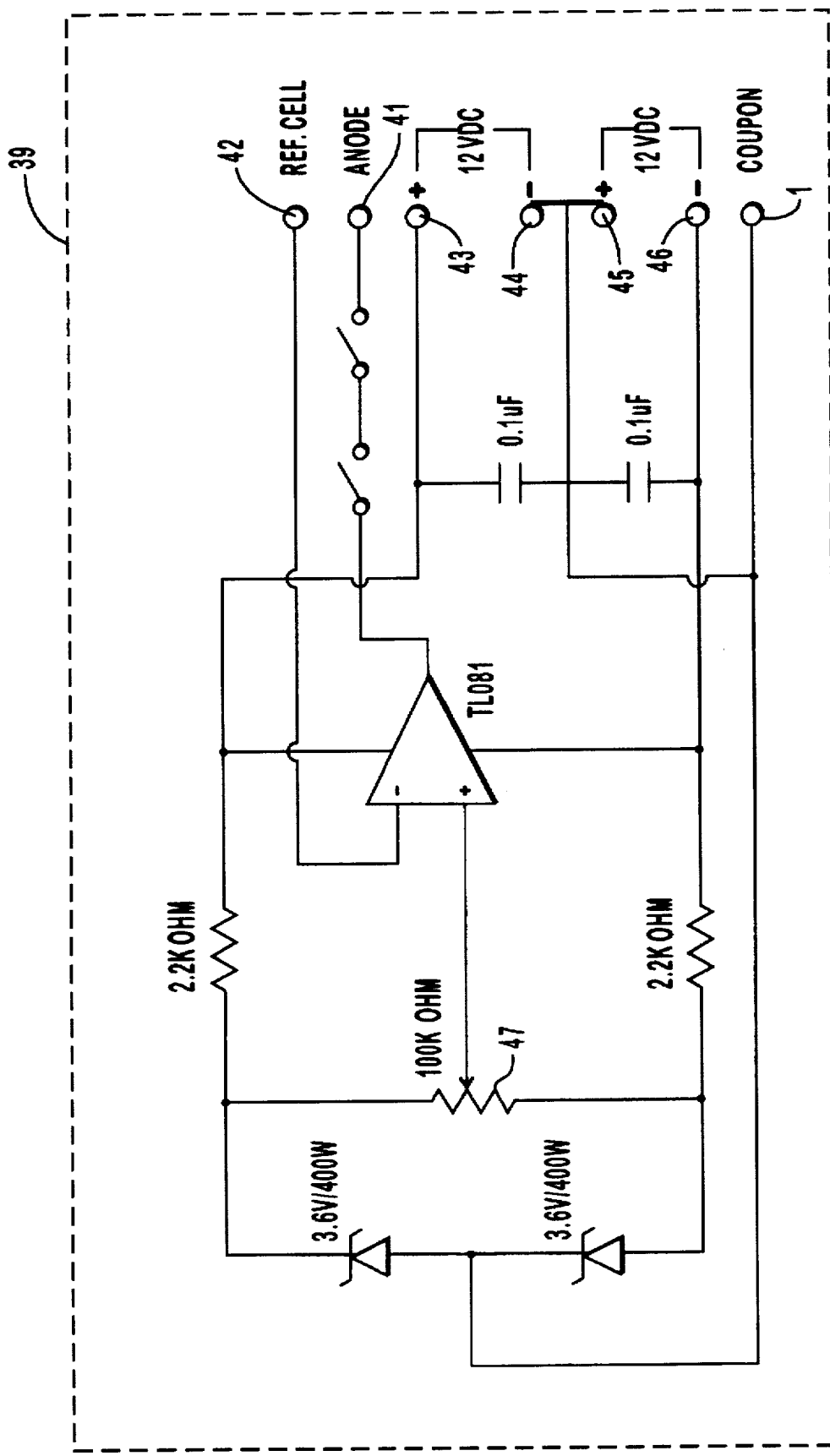
FIG. 4 is a schematic of the potentiostat circuit used in the preferred embodiment of the invention.
Figure 5A:
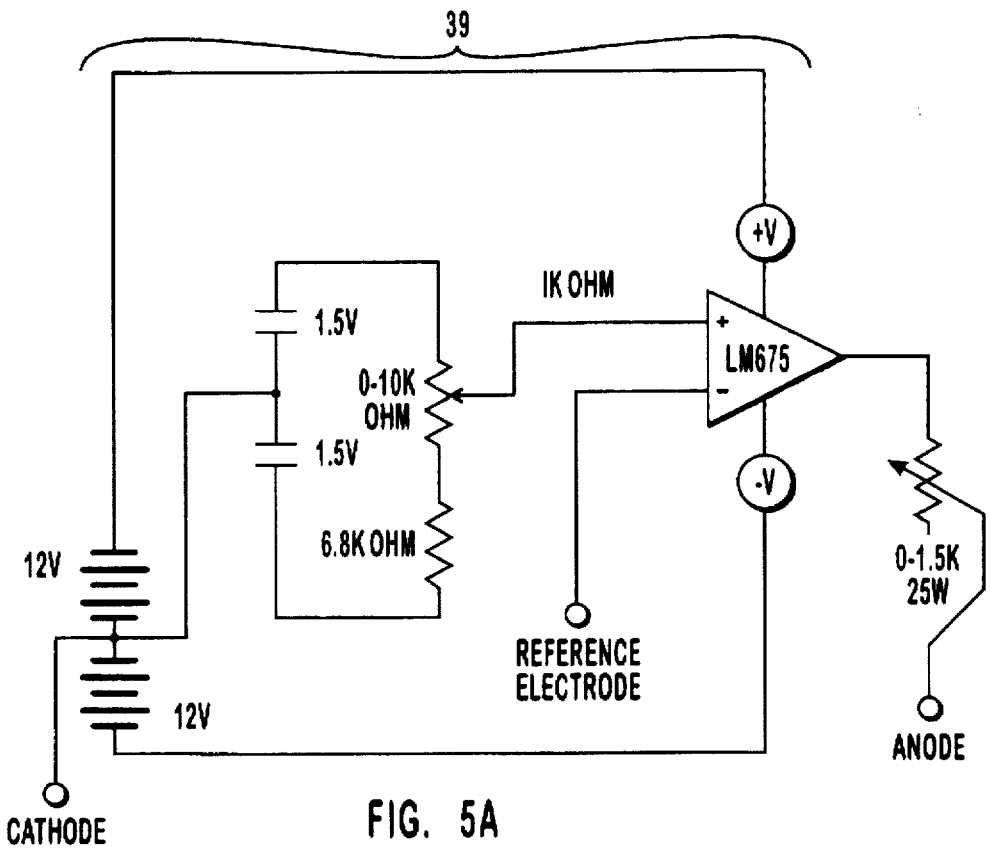
FIGS. 5A, 5B and 5C are schematics of alternative potentiostat circuits which may be used in low-power applications.
Figure 5B:
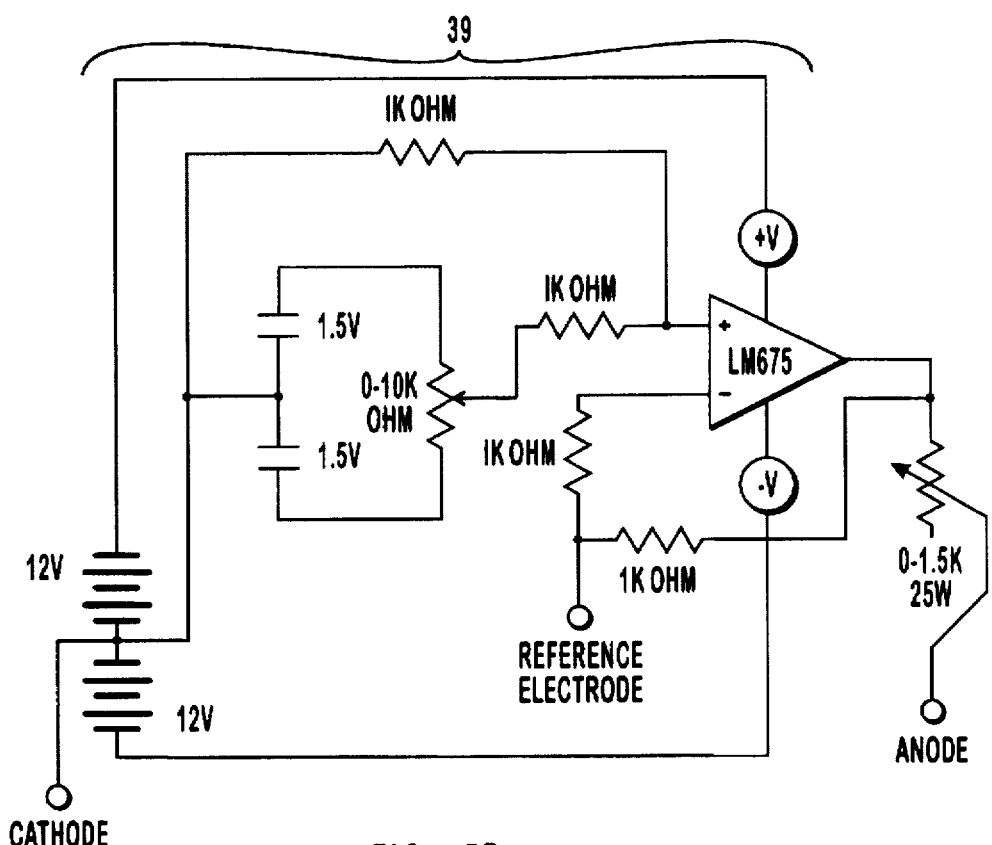
Figure 5C:
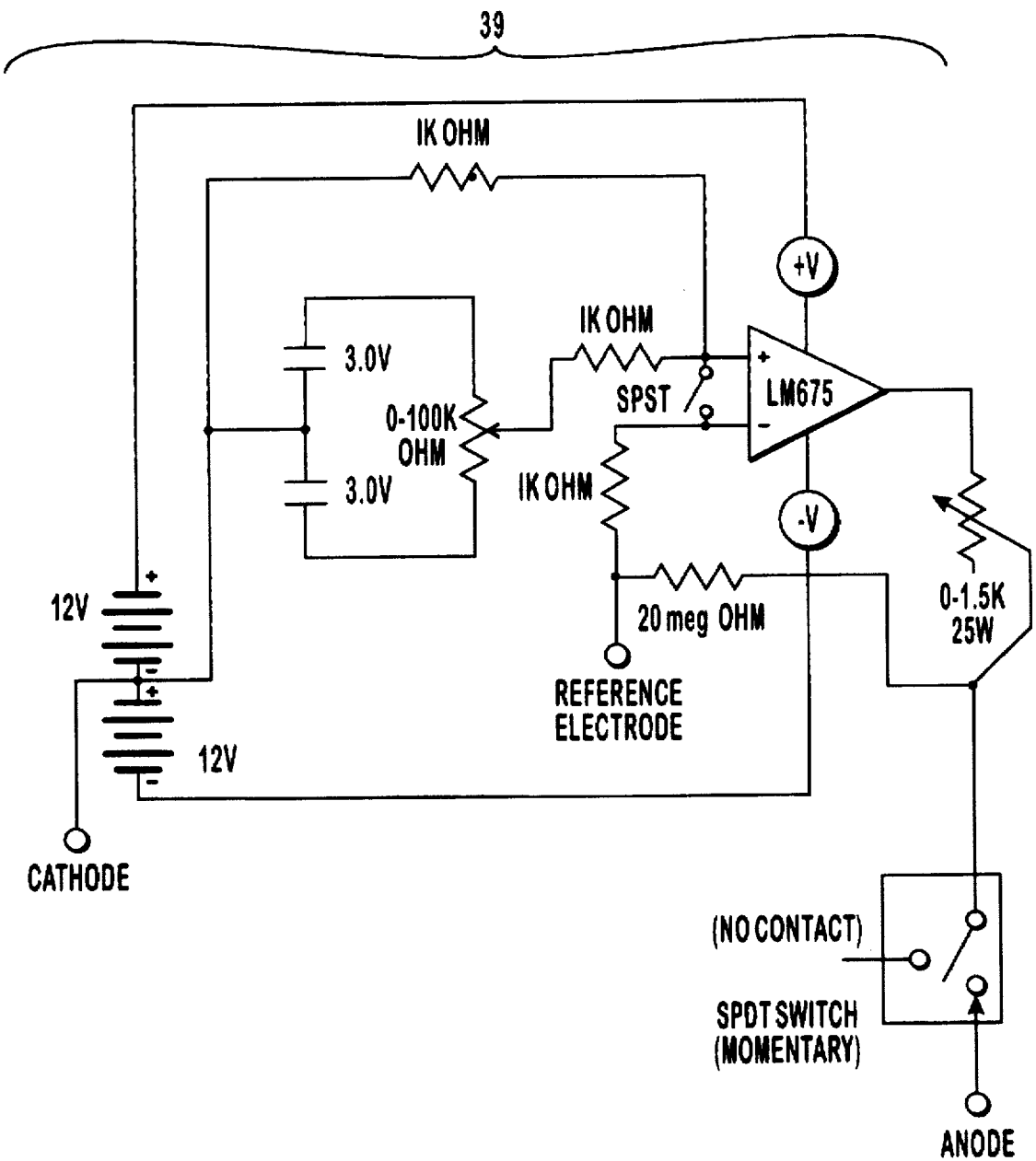

Mini-potentiostats 39 were custom-designed and built for use in the inventive system to provide CP, i.e., a level of polarization on the coupons which will reduce or eliminate SCC. High current requirements for adequate CP of steel in the chosen test environment presented many problems. The op-amp based circuitry presented in FIG. 4 was used in the preferred embodiment of the invention proved acceptable. This circuit was used for all the laboratory tests. Alternatively, in low power applications, the potentiostat circuits shown in FIGS. 5A, 5B and 5C may be used; these circuits provide higher sensitivity in applications where low current levels can be used (i.e. where the coupon surface area is lower, or lower levels of CP are required) but are not sufficient if high current levels are needed. The practice of the invention is not limited to a particular potentiostat design, and any potentiostat which will provide the desired levels of CP may be used without departing from the inventive concept.

Potentiostat 39 is used to provide a selected level of CP to coupon 1. Referring now to the preferred potentiostat shown in FIG. 4, the potential level is varied by adjusting variable resistor 47, which is a 100 k$\Omega$ resistor. The potentiostat adjusts the current between the working electrode (in this case, coupon 1) and a counter electrode (anode 41, which in this case is carbon steel rod) in order to maintain a desired potential between coupon 1 and a stable reference electrode 42, which in the preferred embodiment of the invention is a copper/copper-sulfate cell. Current is provided by two 12 volt DC batteries, which are connected to the potentiostat circuit at inputs 43 and 44, and 45 and 46. Trickle chargers are used to maintain a stable battery voltage for long-term testing.

A separate potentiostat circuit was used with each coupon 1. The 6 levels of polarized potential which were used in this example were −550, −600, −650, −700, −750 and −800 mV vs. a saturated Copper/Copper-Sulfate (Cu/CuSO$_4$) reference electrode 42. This range of values was selected with the expectation that it would bracket the potential range in which SCC can occur. A salt bridge 36 was used to physically isolate the Cu/CuSO$_4$ reference electrode from the hot solution in the test tank 30 (alternatively, a lugging capillary system could be used to isolate the reference electrode). Although 6 potentials were used in the present example of the invention, a larger or smaller number of potentials (and hence coupons) could be used in the practice of the invention.

Environment The selection of a suitable environment for laboratory testing was based on the following requirements. The test electrolyte should be representative of the suspected environment that caused the field cracking. In addition, the test electrolyte in synergism with other necessary factors (stress, level of polarization, etc.) should lead to SCC failure in an accelerated time period. The electrolyte 31 chosen for the laboratory test was a 1N Na$_2$CO$_3$+1N NaHCO$_3$ solution. Tap water and industrial grade chemicals were used during electrolyte preparation. The pH of the solution was measured to be in the 9 to 10 range. The electrolyte was heated to about 140 to 150 degrees Fahrenheit range with immersion heaters 35.

Polarization Measurements

The theoretical model generally proposed to account for IGSCC of pipeline steels is the structurally dependent attack that occurs under active/passive conditions on the metal. Polarization curves have been historically used to identify a critical potential range in which cracking may occur based on a material's active/passive behavior in a given environment. Accordingly, prior to testing for SCC, both anodic and cathodic polarization tests were conducted on X-52 carbon steel in 1N Na$_2$CO$_3$+1N NaHCO$_3$ solution. Active and passive regions were identified, and the influence of the rate of current adjustment, current level, temperature and the scan directions were investigated. By identifying the active/passive transition regions of the polarization curves, the range of potentials at which SCC could be expected to occur were identified. The range of potential values identified herein is thought to be suitable for all pipelines and other structures which are constructed of low-carbon steels such as x-52 or x-60 steel, and if the invention is used to test for SCC in these materials, it would not be necessary to repeat the polarization tests. However, if the invention is to be used for the detection of SCC in structures made of another material, it is preferable to measure polarization curves in order to identify the active/passive transition region and thus range of potentials within which SCC is likely to occur. As discussed in Example 2, it is also possible to measure polarization curves in the field, and in cases where the inventive system is to be installed in the field without first performing lab tests, it may be preferable to measure polarization curves in the field rather than in the lab.

A small X-52 carbon steel coupon was saw cut under water cooled conditions out of the same pipeline section from which the C-type SCC specimens were cut. An electrical connection was made to the coupon by partially drilling through the coupon and threading the hole with a tap. Two wires with soldered termination were mechanically secured to the coupon with a machine screw. The coupon was then cleaned with detergent, rinsed, and then dried. Afterwards, the coupon was encapsulated in a thermoreactive epoxy resin. Encasement of the coupon included all but one side of the coupon. A surface approximately 0.25 square inches remained uncovered. This surface was progressively polished to 400 grit Si-C surface finish, rinsed in tap water, and air dried.

A 1N $Na_2CO_3$+1N $NAHCO_3$ solution was prepared using industrial grade chemicals and tap water. This was chosen as the electrolyte for these tests. The liquid was placed in a glass beaker and heated. After the desired temperature (~150° F.) was attained, the mounted coupon was immersed into the electrolyte.

A three electrode arrangement was used for all polarization tests. The potentiostat circuit shown in FIG. 4 was used. A graphite rod was used as the counter electrode 41. A Silver/Silver-Chloride (Ag/AgCl) was used in the potentiostatic control circuit as reference electrode 42. A $Cu/CuSO_4$ reference electrode was used for measurement purposes. Potentials on the working electrode (i.e., the test coupon) were adjusted manually at a regular rate.

Figure 7:
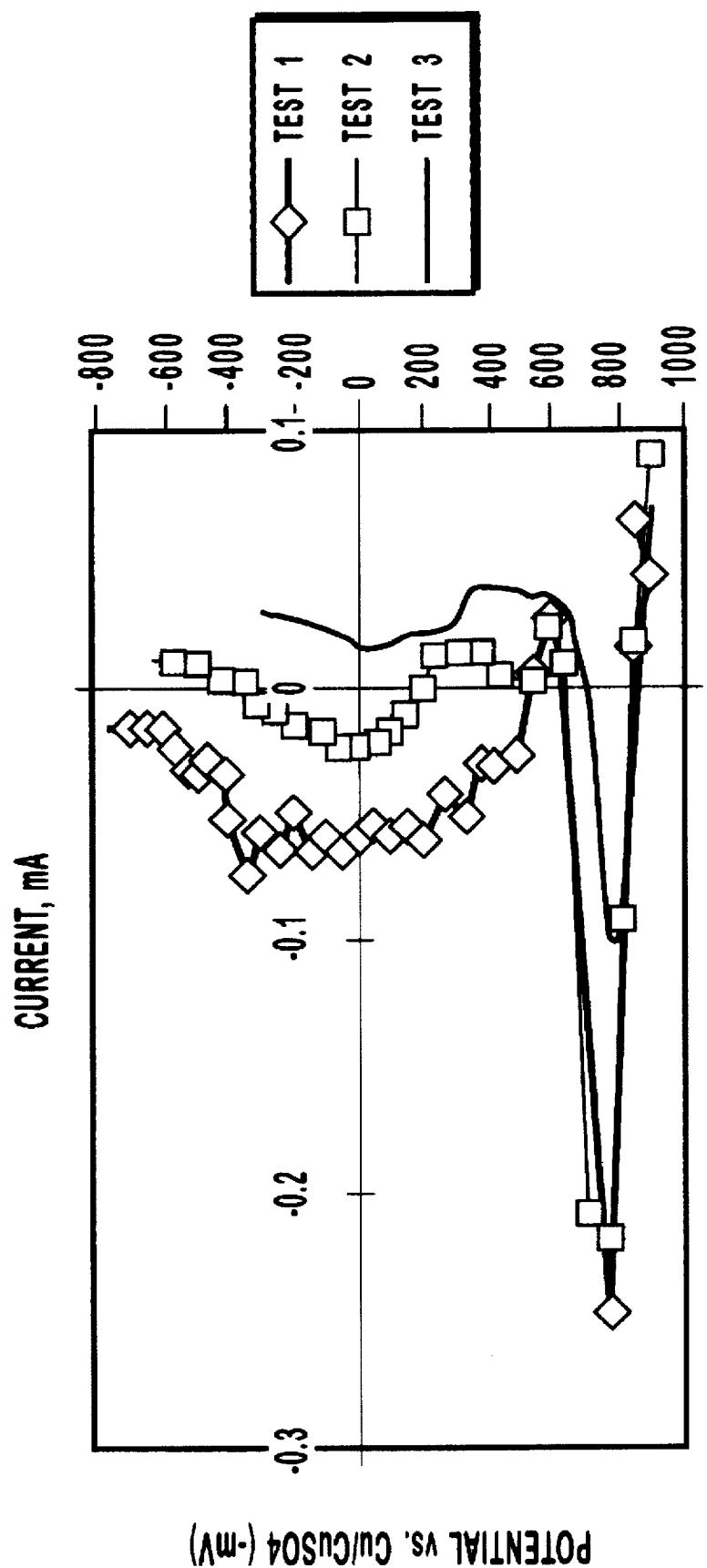
FIG. 7 shows several laboratory anodic polarization curves performed at room temperature at two different manual potential adjustment rates.

A material's corrosion potential is time dependent and a function of the presence or absence of oxide film(s) at the time of immersion. It was observed that the corrosion potential after quasi-stabilization was typically either in the –200 to –250 mV range or –800 to –850 mV range versus a $Cu/CuSO_4$ reference electrode. It has been reported that the more active corrosion potential corresponds to a film-free surface on carbon steel in the environment under consideration. Therefore, most of the polarization tests performed were done so as to force a film-free coupon state at the commencement of the test. This required both cathodic and anodic polarization tests to be commenced at an applied potential of –900 mV vs. the $Cu/CuSO_4$ reference electrode unless otherwise noted FIG. 7 shows anodic polarization curves where potential is plotted vs. applied current with the electrolyte held at room temperature and the current adjusted manually. It can be seen that Test 1 and 2, although performed under similar conditions, show marked variation in response at potentials nobler than the active-passive transition potential. It also appears that the adjustment rate has little effect on the active/passive transition range.

Figure 8:
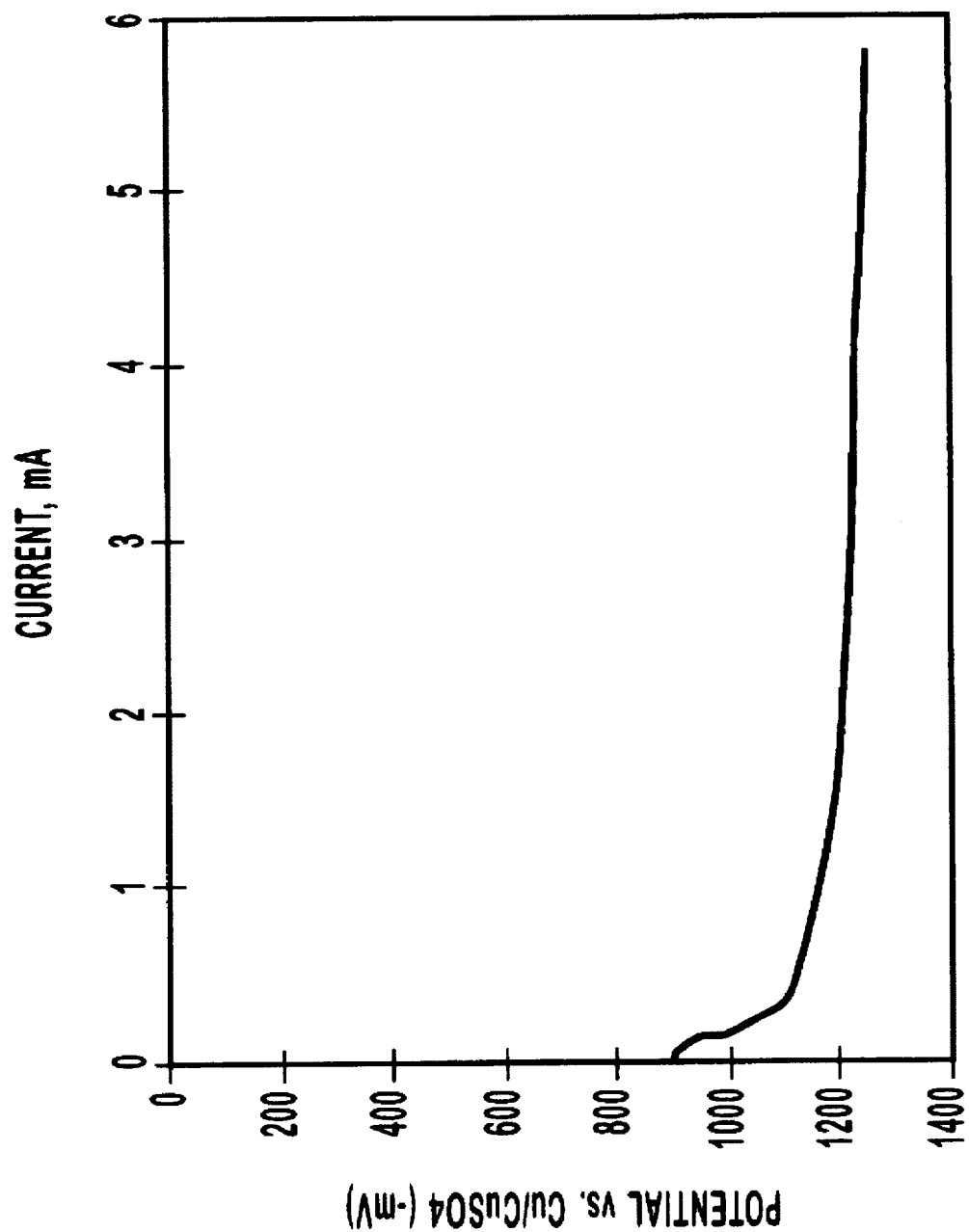
FIG. 8 is a laboratory cathodic potential curve showing the change in potential with respect to change in current.

FIG. 8 shows a cathodic polarization curve where the measured potential is plotted versus the applied current. The electrolyte was held at room temperature and the current adjustment rate was about 50 mV/min (current adjustment rate is given in terms of the rate of adjustment of the supply potential, since the resistance, and hence current, is not known). It appears that beyond a certain level of polarization (around –1100 mV vs. a $Cu/CuSO_4$ reference electrode) the change in potential with respect to the applied current decreases, so that a greater increment of applied current is required to produce even change in potential.

Figure 9:
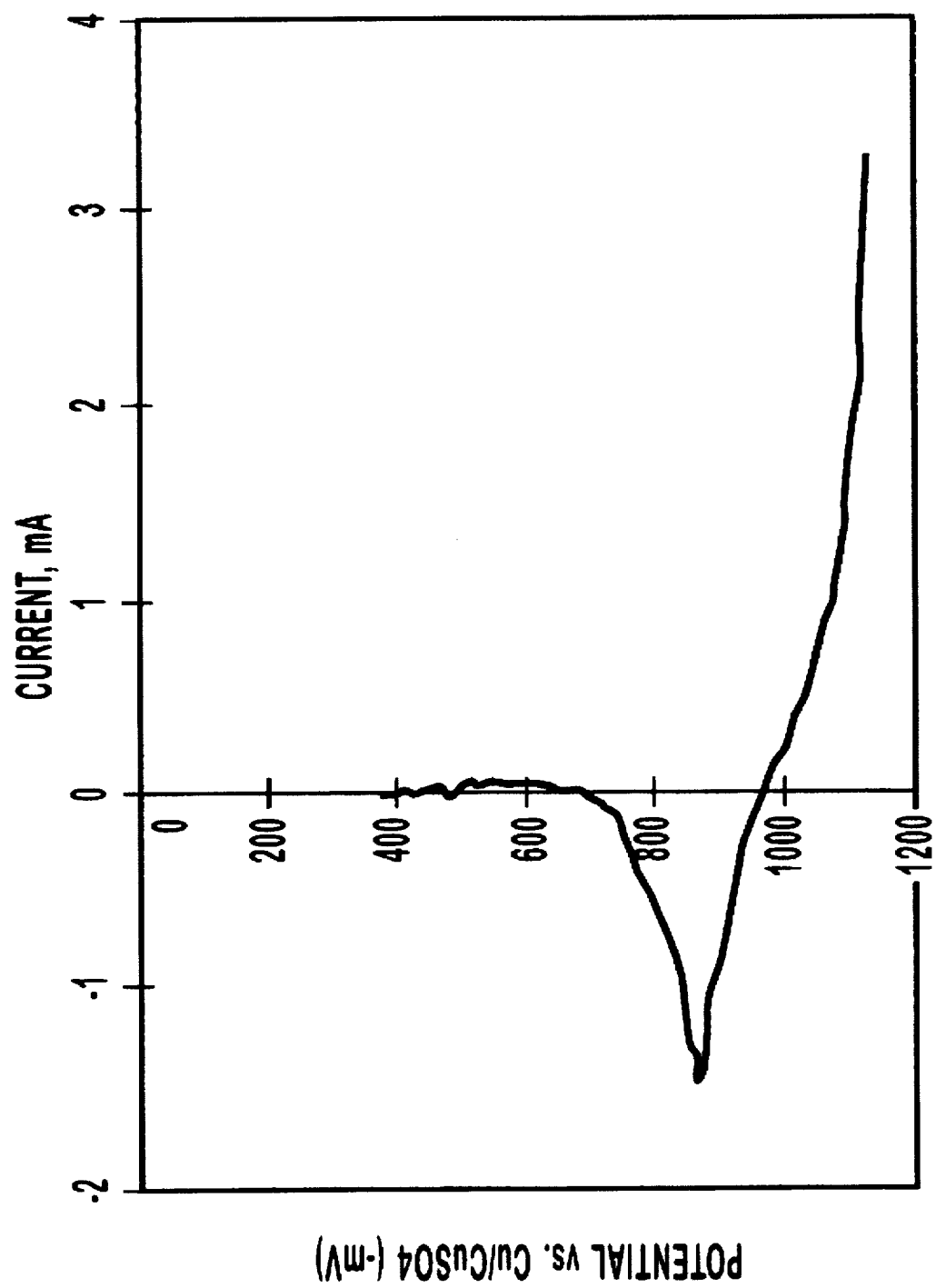
FIG. 9 is a laboratory cathodic potential curve performed at 150 degrees Fahrenheit.

FIG. 9 shows a cathodic polarization curve plotted from data collected with a manual adjustment rate of 10 mV/min and an electrolyte temperature of 150° F. The characteristic transition from a net cathodic to anodic current is observed in the same approximate potential range as observed on anodic curves conducted at room temperature. The cathodic portion of the curve at potentials more active than –950 mV approximates the curve obtained at room temperature. It thus appears that electrolyte temperature has little effect on the electrochemical response of X-52 carbon steel in 1N $Na_2CO_3$+1N $NAHCO_3$ solution. Accordingly, it was concluded that X-52 carbon steel in 1N $Na_2CO_3$ +1N $NaHCO_3$ solution is electrochemically conducive to cracking even at room temperature, other conditions being favorable. This is consistent with the results obtained by R. N. Parkins et al [1]. The rate of cracking or the time to failure will however be accelerated at higher temperatures based on the dissolution controlled model.

Figure 10:
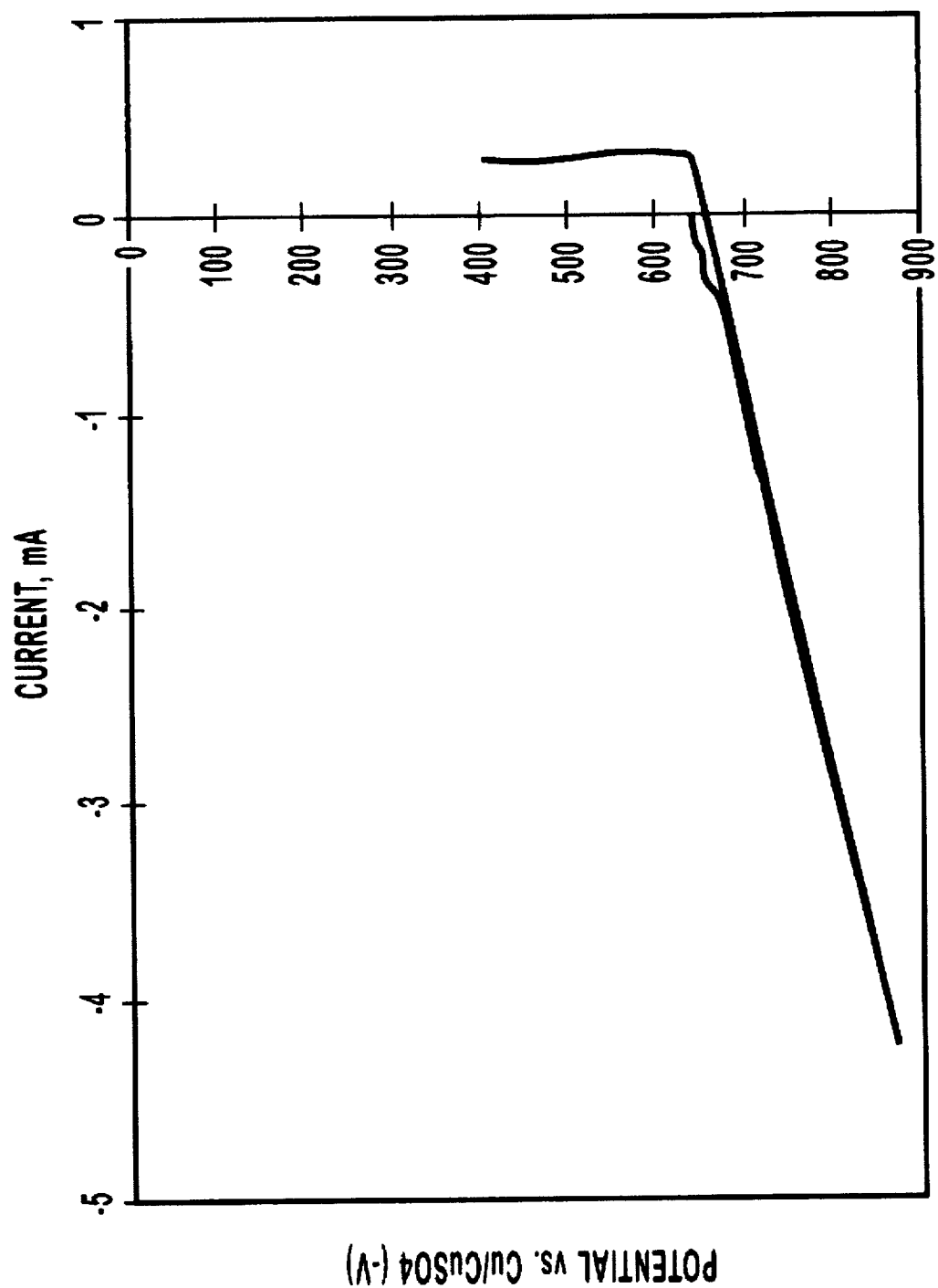
FIG. 10 is a laboratory cathodic/anodic potential curve performed at 150 degrees Fahrenheit.

FIG. 10 shows a cyclic cathodic/anodic polarization curve in the active/passive transition range at around 150° F. The reproducibility of the curve in both anodic and cathodic direction within the active-passive transition range indicates the likelihood that the reactions occurring at the substrate/solution interface are potential specific and not scan direction specific.

Crack Detection

SCC was detected by measuring the change in electrical resistance of the coupon. As cracks are initiated and propagate, the current flow cross-sectional area is decreased, which results in an increase in electrical resistance. A current in the range of 4 to 5 amperes was passed intermittently through each coupon, and the resulting potential drop ($V_{Coupon}$) across the coupon was then evaluated. The potential drop ($V_{Shunt}$) across shunt resistor 22 (shown in FIG. 1) was also measured, and the resistance of the coupon was calculated as the ($V_{Coupon} \times R_{Shunt}$) / $V_{Shunt}$.

Figure 6B:
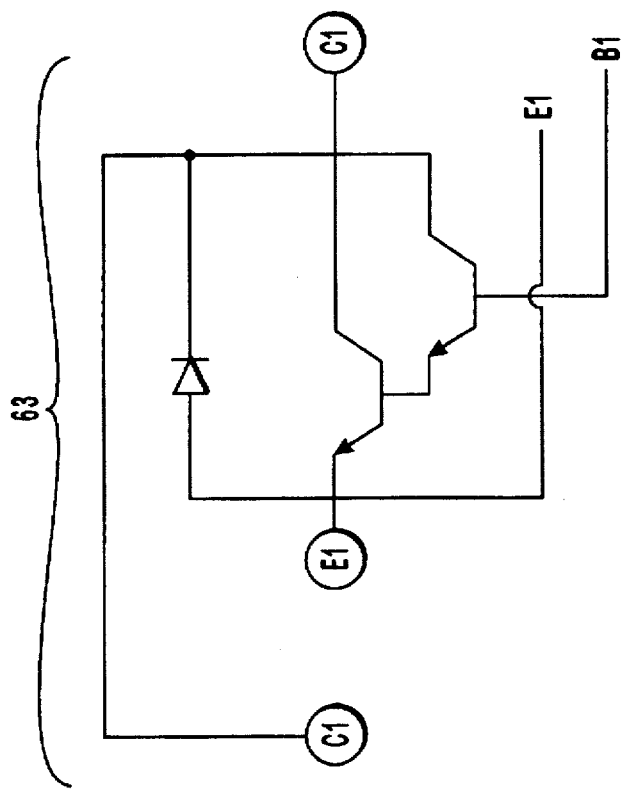
FIG. 6B is a schematic of the transistor used in the crack detection circuit.
Figure 6A:
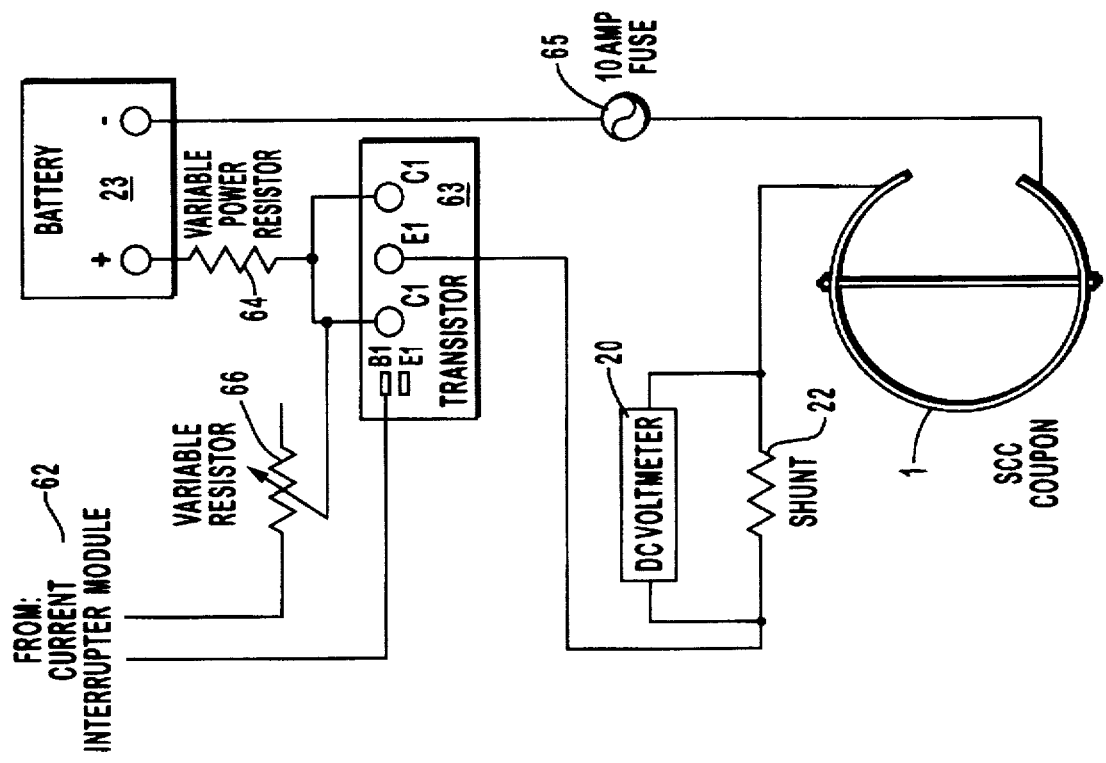
FIG. 6A is a diagram of the crack-detection circuit, showing details of the transistor switch.
Figure 6C:
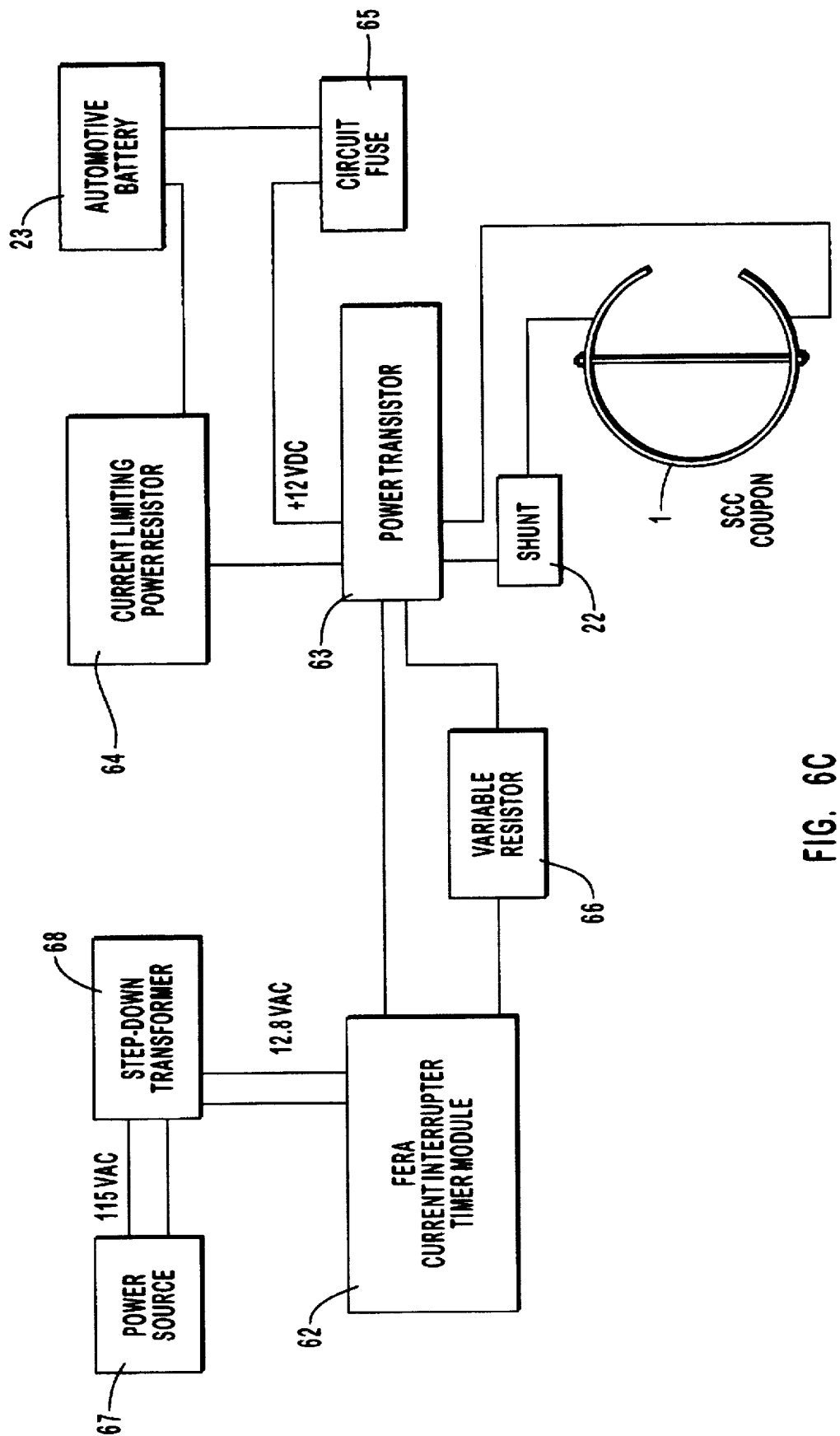
FIG. 6C is an overview of the crack-detection circuit

The crack detection circuitry is presented in FIGS. 6A and 6B. A commercially available automobile battery 23 was used as a current source for the crack detection circuitry. This power source was chosen to have suitable power readily available and still be able to maintain electrical isolation between the six test cells; alternatively, any other current source which met these requirements could be used instead. Current interrupter module 62 was used in combination with the transistor switch 63 to maintain a constant current output, and allow user adjustment of the duty cycle (ratio of current "On" period to total "On" and "Off" period). Current interrupter module 62 provides a gating current to transistor 63, which in turn gates the current from battery 23. The duty cycle used for the test was 10 seconds "On" and 90 seconds "OFF". Variable power resistor 64 and fuse 65 are provided as safety features to limit the current flowing through the coupon and circuitry. Variable resistor 66 allows the level of current flowing through the coupon to be varied. Three 12-volt batteries were used to supply DC power for the six crack detection tests in the laboratory.

Data Collection

Real time data collection in the laboratory tests is done with computer 42 shown in FIG. 3. The 486-33 mHz computer was fitted with a 16 channel, 16-bit Omega Analog to Digital (A/D) PC board was used for data acquisition. Data output from the A/D board and preprocessing was managed by Omega's Quicklog$^R$ software. The frequency of data collection varied with the type of data collected. The highest rate of data acquisition and storage was 1 reading/second taken simultaneously from the 6 different coupons. The data was later processed using MS-Excel$^R$, a spreadsheet style program. The collection of SCC data during the lab tests was primarily for the verification of correct equipment operation; the collection and analysis of SCC data is described in greater detail in connection with field testing in Example 2.

Example 2

Field Testing

There are few methods of field testing for SCC disclosed in the prior art, especially in buried pipeline applications. The present invention is used to address two problems in the field. (1) determine whether current operating and environmental conditions will support SCC; (2) determine the level of CP needed to mitigate SCC.

Sensor Design

Figure 11:
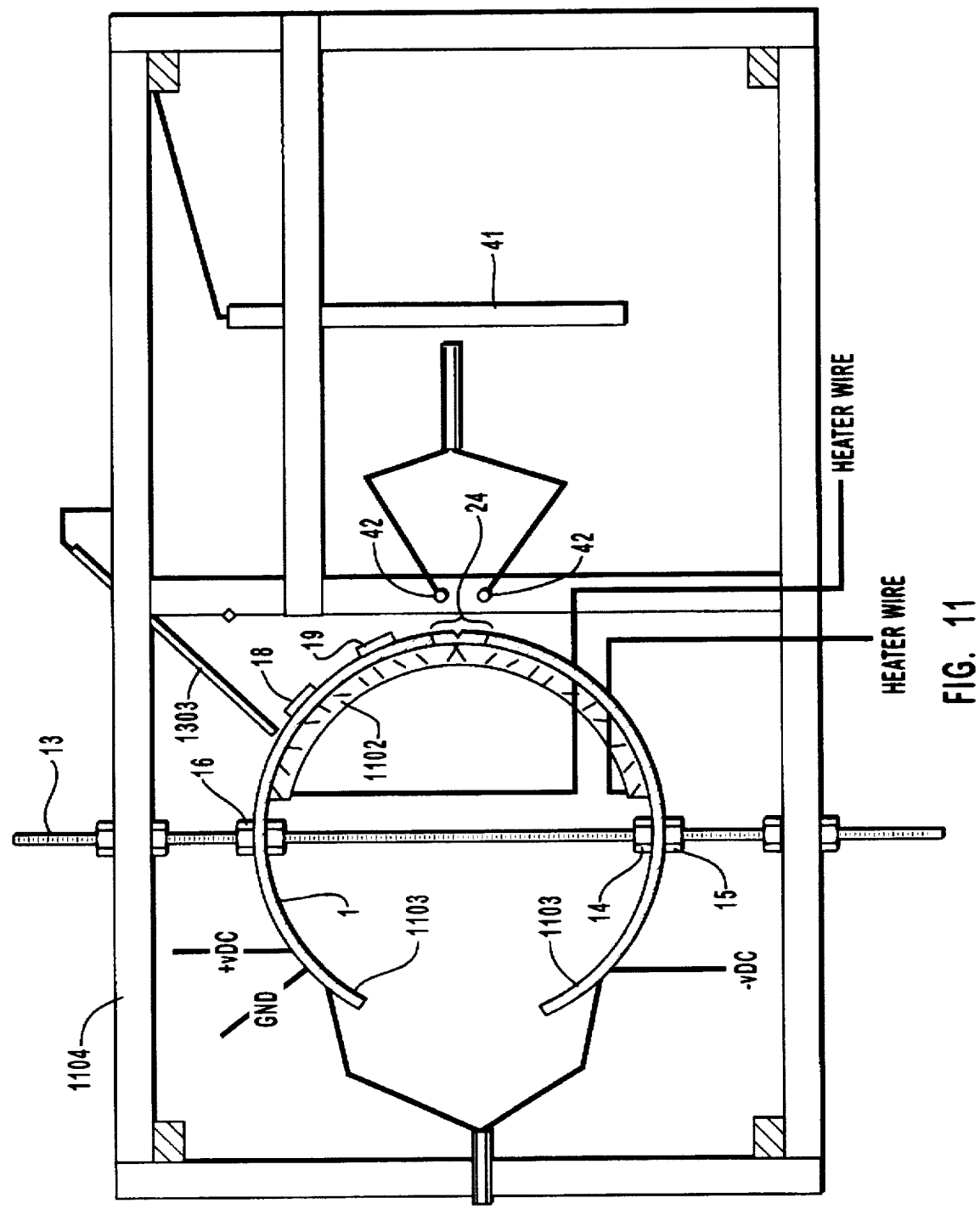
FIG. 11 is a schematic of the sensor used in field testing.

The sensor used in field testing is shown in FIG. 11. Coupon geometry, surface preparation, initial loading procedures, and coating were similar to those described for the laboratory experiment in Example 1. Specific differences were that two strain gauges 18 and 19 were mounted at 50° and 75°, respectively, from the stress axis to determine applied stress levels; the strain gauge located at 25° in the laboratory specimen preparation was eliminated. In addition, after the installation of heat strip 1102 to each coupon, 3M rubber tape was applied to most of the coupon surface. This was followed by the application of 3M +33 vinyl electrical tape helically about the coupon. These wrappings 1103 covered the entire surface of the coupon except for an area 24 of about 2 $in^2$ (on each side of the coupon) centered on the machined notch. This replaced the heat shrink tubing 25 used in the lab testing and served to limit the surface area of the coupon which was subject to corrosion.

Impressed current anode 41 and thermocouple 1303 are also shown in FIG. 11, as are reference cells 42.

The sensor framework 1104 used to support the SCC coupons and their ancillary equipment was designed to sustain long term soil exposure without significant degradation, provide the necessary structural support to sustain the weight of the coupons and their ancillary equipment, and be electrically insulated from the coupons to prevent electrical shorting between the coupons and subsequent degradation of data quality.

Figure 12:
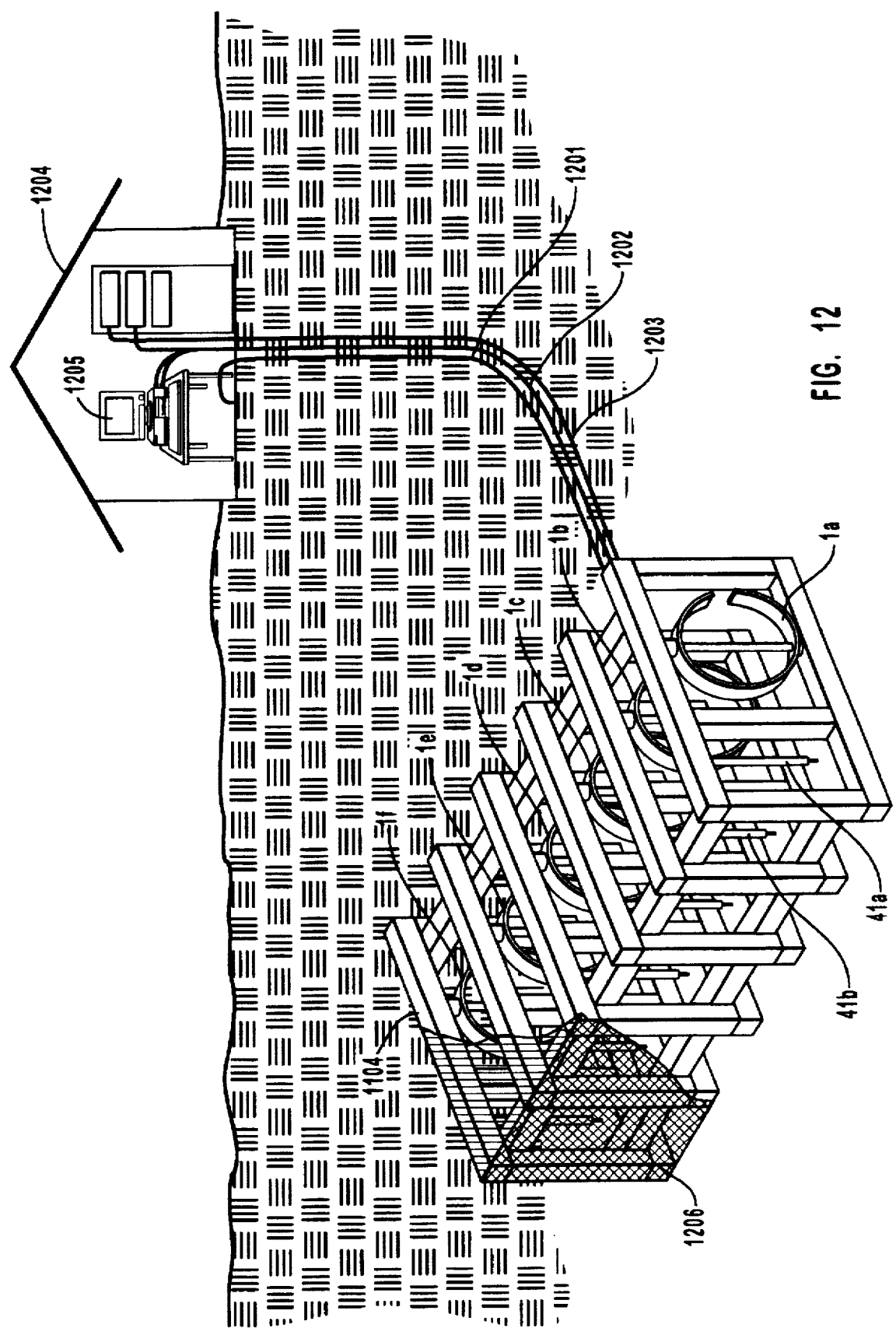
FIG. 12 is an illustration of an embodiment of the invention used in field testing.

Based on the above considerations, square fiberglass tubing was chosen as the fabrication material for sensor framework 1104. The tubing was 2"×2" and had a nominal thickness of 0.25 inches. Each node on the framework was glued with two-part epoxy and bolted together with ¼ inch machine bolts, washers, and nuts. The completed framework with installed coupons and other ancillary equipment can be seen in FIG. 11 (in cross-sectional view) and in FIG. 12 (in perspective view). The framework shown in FIG. 12 supports 6 coupons and their associated equipment. FIG. 11 shows a single coupon and its equipment, which makes up one "test cell". As discussed previously, the number of test coupons (test cells) used in the invention is based on the desired range of CP levels, and the invention is not limited to a particular number of coupons.

Stress

Energy stored in a given material and the environment in which the material is placed contribute to the rate of deterioration. This stress comes from various sources, including the inherent makeup of the material itself, thermally induced microstructural modifications which occurred during manufacturing from machining, rolling and/or welding processes, physical loading due to the operating pressure of the gas flow, cyclic loading arising from changing pressures or applied loading, and soil stresses due to earth movement relative to pipe. Mechanical loading applied to each coupon should be sufficient to cause stress levels higher than observed in normal operations; specifically it is desired to obtain a level which approaches the tensile yield strength for the material being tested. Below this point, elastic deformation occurs and the initiation of a crack in an SCC susceptible environment is much slower or non-existent. However, loading the coupon significantly above this point should be avoided as there is the possibility of excessive plastic deformation and reduction in sensitivity to a SCC promoting environment. In field tests, loading is applied to Coupon 1 by means of nut 16, as described in the lab test setup and preferably with the use of a compression spring 29 to maintain constant stress.

Temperature Control System

Temperature is known to accelerate most chemical and electrochemical reactions. It is inconceivable that the same would not be true in the case of observed SCC on buried pipelines. Temperature variance on the system is generally attributed to system pressure and/or proximity to a compressor station and heat transfer/attenuation characteristics of the coating and surrounding soil. The temperature of each of the coupons in the sensor should initially be controlled at the current operating temperature of the pipeline. This is believed to assist in accelerating the SCC process on the sensor coupons. The system used to control coupon temperatures was designed to enable a remote entity to provide the variable set point and or the capability to have manual control.

Figure 13:
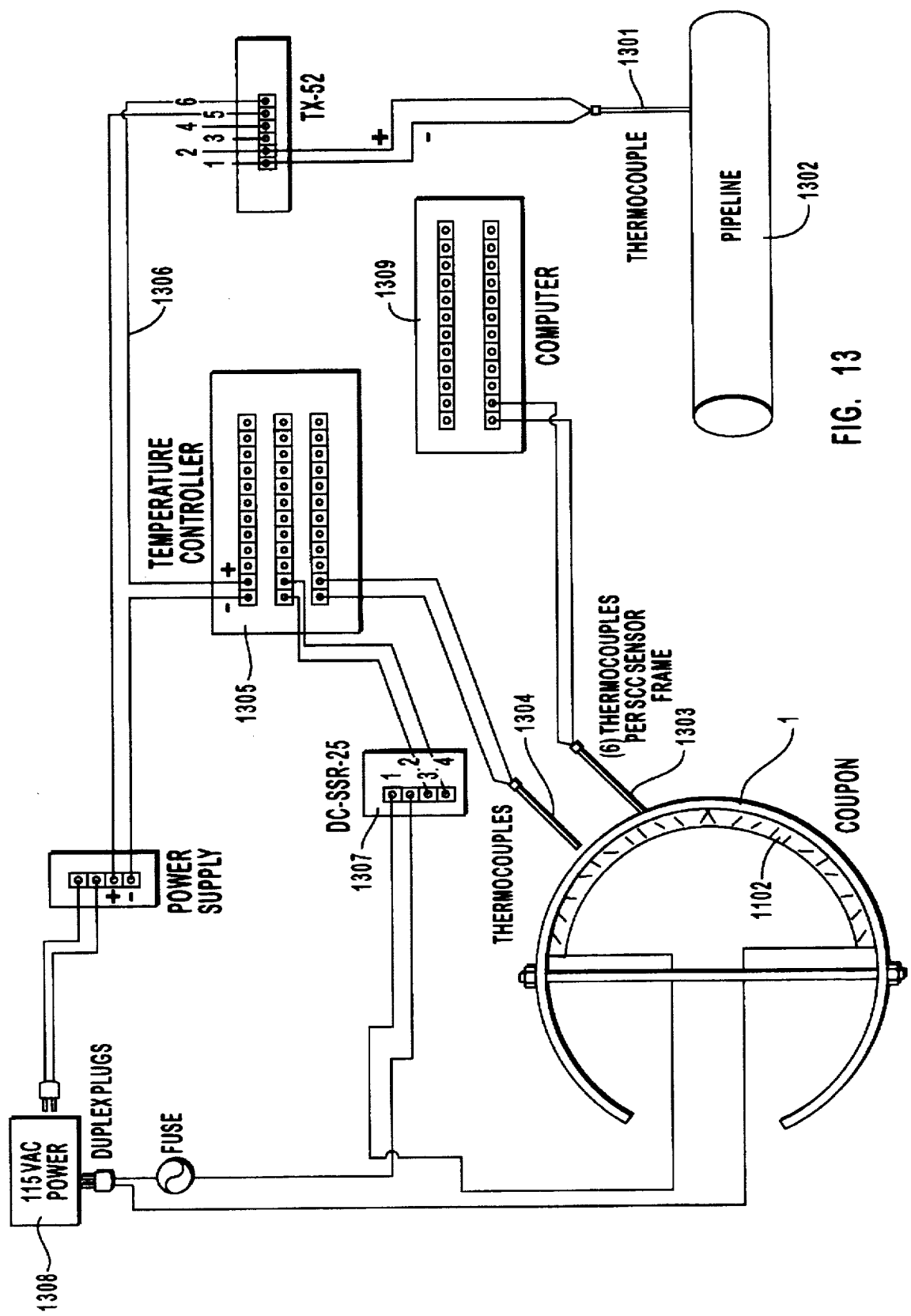
FIG. 13 is a schematic diagram of the temperature control circuit.

FIG. 13 shows a single test cell, representative of all six of the test cells in the sensor. The cell shown in FIG. 13 differs from the other 5 cells only in that 2 thermocouples 1303 and 1304 are shown for measuring the coupon temperature. This is discussed later. The coupon is provided with a flexible heating element 1102 encased in silicone rubber. Flexibility was required to affix the heater to the concave side of the coupon using thermally conductive cement. Silicon rubber was required to limit interactions between the environment and the heater element. The design parameters called for the coupon temperature to be controlled somewhere between 40° and 90° F. Details regarding the chosen heaters are shown below:

| Distributor | Omega Engineering |
|---|---|
| Manufacturer | Kapton |
| Model No. | SRT201-020 |
| Wattage | 209 |
| Watts/In$^2$ | 4.3 |
| Volts | 120 |
| Dimensions | 2" x 24" |

The six heaters used in the sensor were connected in parallel and powered by a single 120 vAC source. These heaters were to maintain each of the coupons at the same temperature.

The temperature control system selected was designed to accept a remote set point input from a "T" type thermocouple 1301 mounted on the pipeline (or other structure) of interest 1302. Alternatively, a manual temperature set point may be used if the current temperature of structure 1302 is not representative (e.g. if it is lower than usual because the pipeline is operating at reduced pressure due to suspected SCC). "T" type thermocouples 1303 were also attached on the coupon 1 in the sensor. One of the coupons was selected for temperature control purposes to be the "master" of the remaining five. The coupon depicted in FIG. 13 is configured as a "master" coupon. The thermocouple 1304 mounted on the "master" coupon was of dual type. This permits the monitoring of temperature as well as providing a voltage signal to the temperature controller 1305 via a 4–20 mA signal generator. Temperature controller 1305 examines the difference between the remote set point on line 1036 and the temperature of master coupon 1304. Based upon this data, the controller sends a signal to an electronic switch 1307 which either closes or opens the 120 vAC power supply 1308 to heater 1102. A temperature control system 1305 supplied by Omega Engineering was used.

| Function | Model |
|---|---|
| Temperature Controller | CN3201TC1-DC-RSP |
| Thermocouple Transmitter | TX-52 |
| Solid State Relay | SSR240DC25 |
| Power Supply | U24Y101 |
| T Type Thermocouple | TJ1200-CPSS-116V-18 |
| Dual T Type Thermocouple | TJ1200-CPSS-116V-18-Dual |

Any comparable temperature control system could be used.

Since temperature significantly affects the SCC tendency of buried pipelines, a history of the daily and seasonal temperature profile is necessary to prevent future long term exposure of the pipe to critical temperature conditions. The temperature attenuation characteristics as a function of distance from a compressor station is important in defining the physical length of pipe that needs monitoring more so than the rest of the pipe with regards to the risk of SCC. However, it is to be noted that there is always a possibility of some other parameter besides temperature being a rate determining step that could lead to SCC at extended distances from a compressor station.

Potential Control System

Figure 14:
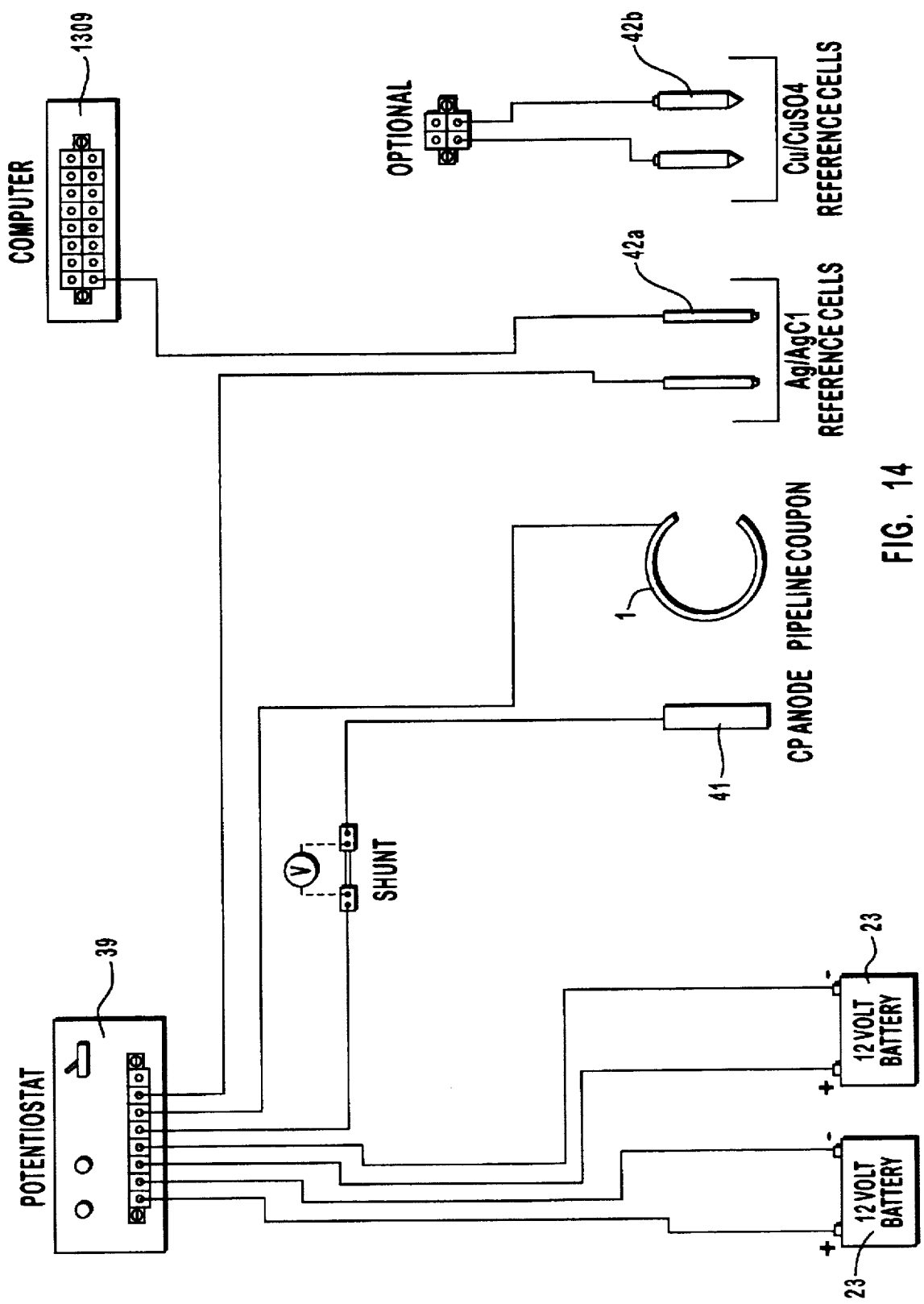
FIG. 14 is a schematic diagram of the circuit used to generate cathodic protection.

The levels of polarization on the coupons in the sensor should be distributed in a range generally believed to sustain SCC, other conditions being favorable. A large range of potentials can be examined. In this example, levels of −550, −600, −650, −700, −750, and −800 mV vs. a Copper/Copper-Sulfate reference cell were selected. These desired potentials dictated the need for six coupons to be located on each sensor. The invention is not limited to a particular number of coupons; a larger or smaller number of coupons could be used as warranted by the expected range of potentials at which SCC might occur. The system used to maintain individualized potentials on each of the coupons is similar to that described for the lab testing is shown in FIG. 14. Each coupon 1 is provided with an independent potential control circuit to prevent electrical shorts between the coupons. Similarly, each coupon has its own impressed current anode 41 to provide the needed CP current. Anodes 41 are FW type Duriron anodes, 1⅛" OD×9" long. These anodes have approximately 1 lb. of consumable material and should last well beyond the scope of the project. Two double junction, sealed Ag/AgCl reference electrodes 42a were installed for each coupon. One of the electrodes is used as the primary reference source for the potentiostatic circuitry. The other reference cell is used as a system backup. Each sensor had two Copper/Copper-Sulfate reference electrodes 42b installed to provide initial potentials for cross reference to the Silver/Silver-Chloride electrodes. The copper-based reference cells were not used for continued testing because of potential susceptibility to contamination. Polarized potentials are measured by momentarily shutting off CP currents to obtain "instant off" potentials which reflect the true polarization potential.

At all three monitoring sites, high electrolyte IR drops in the hundreds of mV range were observed. The electrolyte IR drop was created as a combination of mutually interacting electric fields of the coupon's cp system and/or due to earth current effects. This made it difficult to estimate the "true" polarized potential of the coupons. Regular current interruption tests were conducted to adjust the "On" potential of the coupons in order to obtain the desired "Off" potentials.

Crack Detection System

Figure 15:
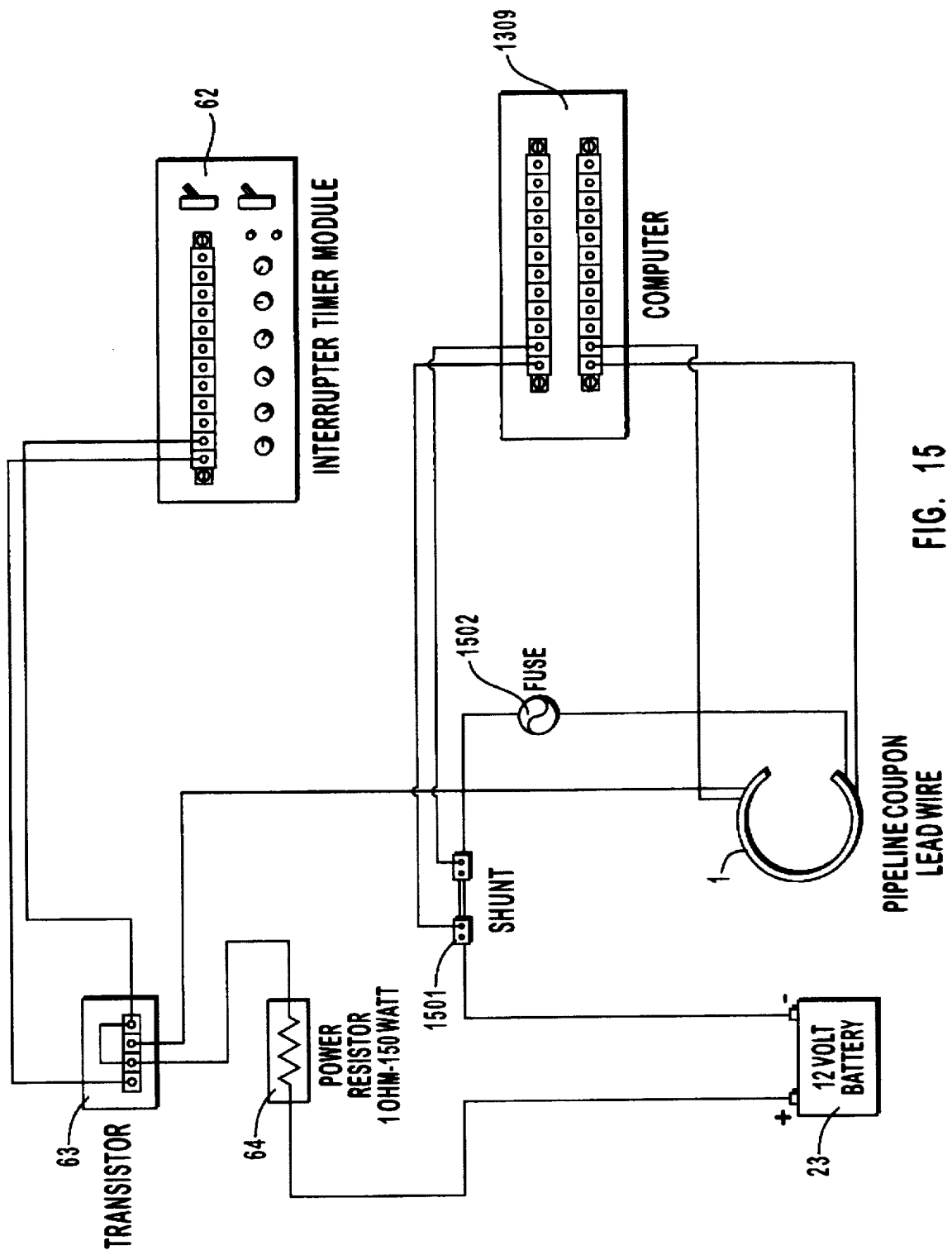
FIG. 15 is a schematic diagram of the crack detection circuitry used in field testing.

The crack detection circuitry was similar to that previously described for the laboratory experiment. However, a single controller [interrupt timer] with multi-channel outputs was custom built to lessen the number of components in the system. The crack detection circuitry used in field testing is shown in FIG. 15. As in the laboratory experiment, controlled DC current from individual, heavy duty automobile batteries flows through each coupon for a "short" period of time. The applied current is calculated using Ohm's law from the voltage drop across a precision shunt 1501 and the coupon resistance is calculated from the measured voltage drop across the coupon as a result of the applied current. Each coupon is independent of the other five.

Data Acquisition

A computerized data acquisition system was installed at each site. The design weighed heavily upon the fact that the field sites were remote from the staffed offices. The system was based about pentium computers, Gateway 2000 P5-90 systems which have 750 MB hard drives. Into each computer were installed two Omega Analog-to-Digital (A/D) cards. The primary card, #WB-AAI-B16, is a 16 bit board with 16 independent channels. The secondary card, #WB-FAI-B16, is a 12 bit board also with 16 independent channels. The following table presents channel usage details for the two A/D boards:

| Data Acquisition | A/D Board | Channels |
|---|---|---|
| Crack Detection System | 16-Bit | 1 thru' 12 |
| Potential Monitoring System | 16-Bit | 13 thru' 16 |
| Potential Monitoring System | 12-Bit | 1 thru' 8 |
| Temperature Monitoring System | 12-Bit | 9 thru' 14 |

Each computer system has Windows® 3.1 and several application programs installed. Also installed is WorkBench for Windows®, a data acquisition software package marketed by Omega Engineering. Using this software, a custom data acquisition program was assembled allowing data to be collected at different intervals depending upon type in a continuous fashion, seven days a week and 24 hours per day. Tied to a telephone system, the data acquisition computers with their built-in modems are polled daily from the staffed offices to recover the previous day's data. These data are preprocessed with custom software and examined for engineering interpretation.

Data from the crack detection system was acquired over a period of seventeen minutes every hour at a frequency of one herts. The data acquisition window enclosed the cycle period of the current interrupter setting used. Since current flow through the coupons occurred during a small interval of the interrupter cycle perio (and therefore the data acquisition), significant crack detection data formed only a small portion of the data acquired. In order to filter out data corresponding to no current flow through the coupons, a simple filter was established in MS-Access (Version 2.0), a datbase program. The output of the filter comprised of shunt and coupon potential drop data for the six coupons during the course of the data acquisition period when current flow through the coupons occurred.

Coupon resistance was obtained by dividing the voltage drop across the coupon by the voltage drop across the shunt and multiplying by the shunt resistor value. The result was presented in a MS-Excell (Version 5.0) format on a weekly basis as average resistance, minimum resistance, maximum resistance, standard deviation, slop in the resistance data and the slope angle for the period. Sample resistance data are presented in Table 1. In the event of cracking, the coupon's resistance should increase as a function of the depth of the crack. It is

TABLE 1

Crack Detection Analysis

| Parameter | 12/28/95 Coupon 1 | 12/29/95 Coupon 2 | Coupon 3 | Coupon 4 | Coupon 5 | Coupon 6 |
|---|---|---|---|---|---|---|
| Average Resistance (micro-ohm) | 586 | 609 | 639 | 597 | 597 | 587 |
| Minimum Resistance (micro-ohm) | 561 | 591 | 592 | 583 | 572 | 370 |
| Maximum Resistance (micro-ohm) | 606 | 632 | 689 | 615 | 612 | 608 |
| Standard Deviation (micro-ohm) | 8 | 7 | 14 | 6 | 8 | 19 |
| Slope | −0.0388 | −0.0553 | −0.0704 | −0.0427 | −0.0390 | 0.0081 |
| Slope angle (degrees) | −2.2202 | −3.1628 | −4.0251 | −2.4470 | −2.2314 | 0.4628 | believed that the cracking phenomenon, unlike uniform corrosion, would be discontinuous in nature, so that following the resistance variation trend would aid in the differentiation of the two. It is to be expected that variation in the temperature of the coupon either because of the heater turning on or due to current flow through the coupon or both could lead to small variations in the coupon's resistance. Therefore, statistical data on resistance were used to quantify the variation in coupon resistance during a weekly period. Comparison of these parameters at the beginning of the installation, when no crack was present, to corresponding values a few weeks or months later (when cracking could have occurred) would aid in the differentiation of cracking-relatied coupon resistance change from normal temperature related effect. The parameters "slope" and "slope angle" are used to see if a trend exists in the coupon resistance data. A consistent positive increase in the slope would indicate the occurrence of cracking.

Potential data was analyzed on a daily basis. The average, maximum, minimum, and standard deviation for six coupons, measured with both the primary and secondary reference electrodes, are shown in Table 2. A stable polarized potential is essential to initiate and sustain cracking. A standard deviation of less than 10 mV is preferred in the principal "On" potential value.

Temperature data was also analyzed on a daily basis. A sample of temperature data is shown in Table 3. A monthly report which shows temperature, resistance, and potential data for a 1 month period is shown in Table 4.

TABLE 2

Polarization Monitoring

| | Specimen 1 | | Specimen 2 | | Specimen 3 | | Specimen 4 | | Specimen 5 | | Specimen 6 | |
|---|---|---|---|---|---|---|---|---|---|---|---|---|
| | Principal | Backup | Principal | Backup | Principal | Backup | Principal | Backup | Principal | Backup | Principal | Backup |
| Average (mV) | 546 | 597 | 567 | 543 | 680 | 1042 | 788 | 1385 | 866 | 748 | 980 | 947 |
| Maximum (mV) | 573 | 834 | 604 | 574 | 720 | 1079 | 818 | 1437 | 899 | 841 | 1016 | 1085 |
| Minimum (mV) | 537 | 506 | 554 | 530 | 668 | 893 | 0 | 1319 | 854 | 728 | 0 | 927 |
| Std. Dv (mV) | 5 | 110 | 6 | 5 | 6 | 11 | 24 | 11 | 7 | 11 | 30 | 15 |

TABLE 3

Temperature Analysis

| | Coupon 1 | Coupon 2 | Coupon 3 | Coupon 4 | Coupon 5 | Coupon 6 |
|---|---|---|---|---|---|---|
| Average Temperature | 49.74 | 50.81 | 49.89 | 50.35 | 50.43 | 50.65 |
| Maximum Temperature | 51.30 | 52.40 | 51.40 | 52.00 | 51.90 | 52.30 |
| Time @ Max. Temperature | 14:35:11 | 14:35:11 | 13:15:11 | 13:15:11 | 13:15:11 | 14:35:11 |
| Minimum Temperature | 48.40 | 49.50 | 48.60 | 49.00 | 49.20 | 49.30 |
| Time @ Min. Temperature | 10:15:11 | 10:15:11 | 10:15:11 | 10:15:11 | 10:15:11 | 10:15:11 |
| Median Temperature | 49.70 | 50.70 | 49.75 | 50.20 | 50.30 | 50.50 |

TABLE 4

| | Summary Data | | | |
|---|---|---|---|---|
| Dates | 11/16/95 | to | 12/15/95 | |
| Std. Dev | 1 | 2 | 1.24 | 1 |
| Average | 507 | 474 | 52.84 | 578 |

| Date | Principal P/S Potential, mV | Backup P/S Potential, mV | Average Temperature, deg. F. | Average Resistance, micro-ohms |
|---|---|---|---|---|
| 11/16/95 | 506 | 473 | 54 | |
| 11/17/95 | 506 | 494 | 54 | |
| 11/18/95 | 506 | 475 | 54 | |
| 11/20/95 | 506 | 476 | 54 | |
| 11/21/95 | 507 | 476 | 54 | |
| 11/22/95 | 506 | 476 | 54 | 579 |
| 11/23/95 | 506 | 476 | 54 | |
| 11/24/95 | 505 | 477 | 54 | |
| 11/25/95 | 506 | 476 | 54 | |
| 11/26/95 | 507 | 475 | 54 | |
| 11/29/95 | 506 | 471 | | 579 |
| 11/30/95 | 506 | 473 | 53 | |
| 12/1/95 | 507 | 472 | 53 | 579 |
| 12/2/95 | 507 | 472 | 53 | |
| 12/3/95 | 507 | 473 | 53 | |
| 12/4/95 | 508 | 473 | 53 | |
| 12/5/95 | 508 | 475 | 53 | |
| 12/6/95 | 508 | 475 | 53 | 578 |
| 12/7/95 | 508 | 475 | 53 | |
| 12/8/95 | 509 | 476 | 52 | |
| 12/9/95 | 509 | 476 | 52 | |
| 12/10/95 | 508 | 477 | 52 | |
| 12/11/95 | 507 | 473 | 51 | 578 |
| 12/12/95 | 506 | 473 | 51 | |
| 12/14/95 | 507 | 471 | 50 | |
| 12/15/95 | 507 | 469 | 50 | 577 |

Sensor Installation

Criteria which must be considered in locating a site for SCC sensors include: distance relative to prior failure location(s) during hydrostatic testing, proximity to compressor station, right-of-way considerations, landowner(s) approval, power/communication availability, and accessibility of the site.

The preferred location for the sensor is one which replicates the environment at the existing system. Therefore, in this example, it was decided to bury the sensor at the approximate depth of an existing pipeline. In all cases, the sensor was to be buried approximately 10 feet away from the centerline of the pipeline at its closest point to minimize disturbances to the pipeline. This lateral location between the sensor and the pipeline is an acceptable compromise between achieving remoteness from the latter to avoid large potential gradients and right-of-way limitations.

The environment placed about the sensor and/or its nested coupons is all-important to the project. Soil surrounding a buried pipeline has many characteristics which can vary from point to point on the system. Each of these may affect the potential for interaction between the environment and the structure. Most notable of these are: Composition, pH, and porosity. Accordingly, it is preferred to use material excavated during the installation of the sensor as backfill. Although other materials may be easier to locate about the sensor, there exists the possibility that these alien materials would not achieve common attributes with sufficient time. Any deviation from the local conditions could bias the results of the testing. Excavation and backfilling of the site should also be done so as to ensure minimal disturbance to natural soil composition and distribution. However, large rocks or other dense material which potentially could cause physical damage to the sensor during installation should be removed.

The procedure for installing the sensors in the field was as follows: Trenching was accomplished at each of the sites using a rubber tired, hydraulically actuated backhoe. After digging with the backhoe and hand shoveling to uncover the pipeline, a thermocouple was attached for system control. The continuous lead wire set from the thermocouple was place in PVC conduit and buried across the right-of-way to the hole dug for the sensor. The sensor was lowered into the hole placing the coupons at the same depth as the pipeline and offset by approximately 10 feet. Wiring from each of the coupons in the sensor were grouped by function (i.e., power, control, or signal monitoring). (See lines 1201, 1202 and 1203, respectively in FIG. 12). These wire groups were separated and placed in PVC conduit installed between the sensor and the building 1204 which housed the data acquisition equipment 1205. After the wiring between the sensor and the building was completed, the sensor was encapsulated in a galvanized wire mesh 1206 used for fencing. This was required to serve as a sieve to remove the largest of the rocks found in the excavation materials. These were of sufficient size to damage the sensor during the backfilling operation.

Suitable housing was fabricated on-site to protect the necessary data acquisition hardware from the elements. These were wooden framed, metal sheathed structures fixed on performed concrete pads. The invention is not limited by the housing—it is well-known to those of ordinary skill in the art to construct casing, housing, etc. as needed to protect measurement equipment.

After sensors were installed, the necessary wiring connections were made in the building. All of the electrical wiring from the sensor were terminated on a master board mounted on the wall of each room. Termination strips, signal processing equipment, and other devices were also mounted on this board. Each board had more than 500 wiring connections which were initially terminated with compression fittings and then soldered to lessen environmental problems which might be encountered during the tests. It was decided that boards are preferably prewired before they are brought to the field site. This would lessen wiring problems and greatly shorten the installation time required.

Connections to the different process control and/or data monitoring instruments was as per circuit diagrams discussed earlier.

It should be noted that in some cases it may be preferred to install sensors at multiple sites along a pipeline, for example in the case that a number of different environments were suspected of causing SCC. The invention is not limited by the number of installation sites; as more sites are used, it is simply necessary to provide the measurement equipment described herein, in connection with a single sensor, at each site.

Monitoring

Figure 16:
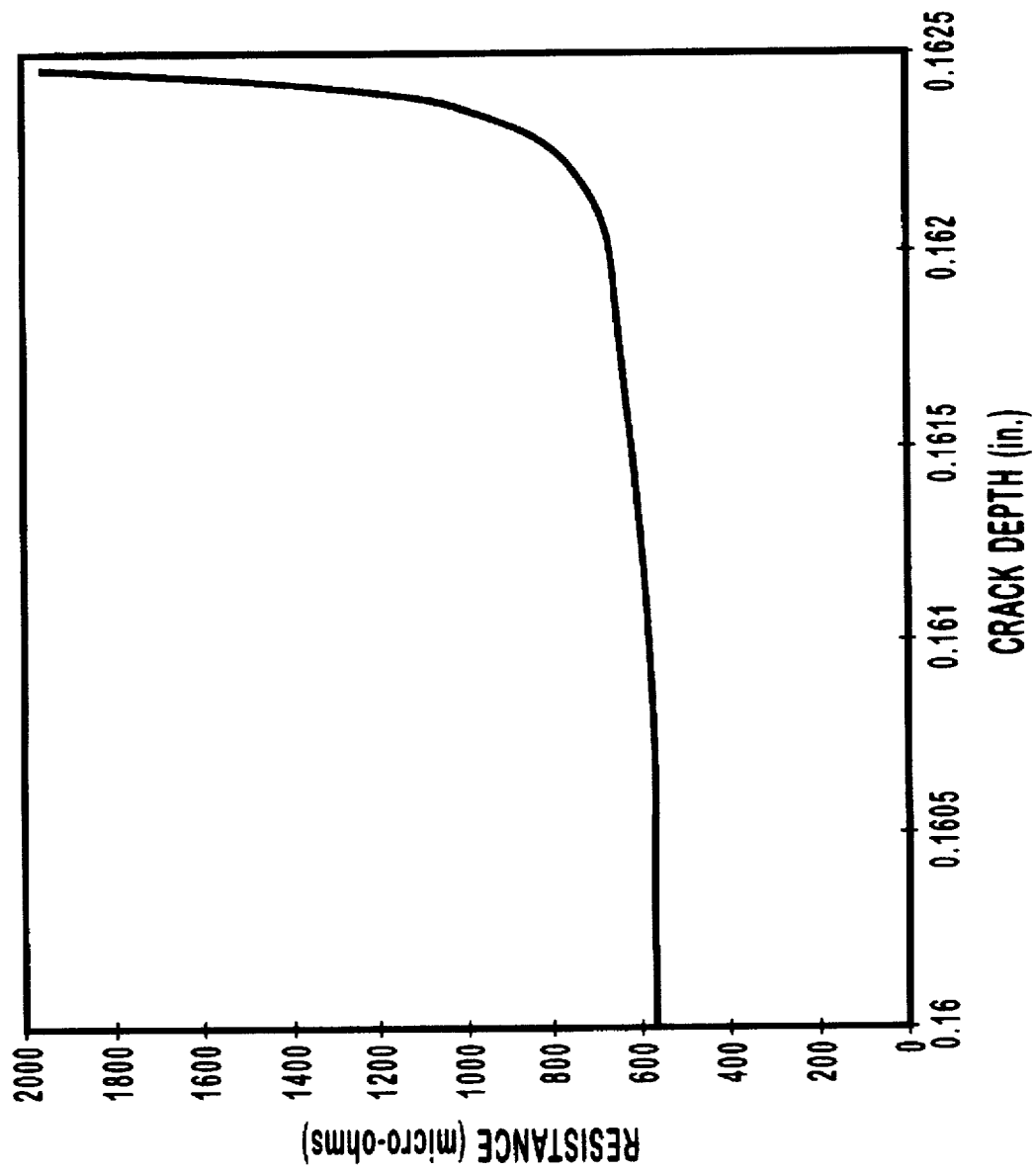
FIG. 16 is a plot of predicted resistance versus crack depth.

The progression of SCC was monitored based on changing electrical resistance consequent to crack growth. Based on the magnitude of current flow to the test coupons and the resulting coupon IR drop, the coupons' electrical resistance was evaluated. The expected variation in coupon resistance with crack propagation is presented in FIG. 16. The variation of electrical resistance was documented for the test coupons at each of the three sites and typical ones are presented in Tables 4 and 5. The weekly summary was ideal to obtain a historical perspective on coupons' electrical resistance variation.

The monitoring procedure and data presentation formats can be performed routinely in a semi-automatic way by a technician level person with regular review by an engineer.

Polarization Measurements

Figure 17:
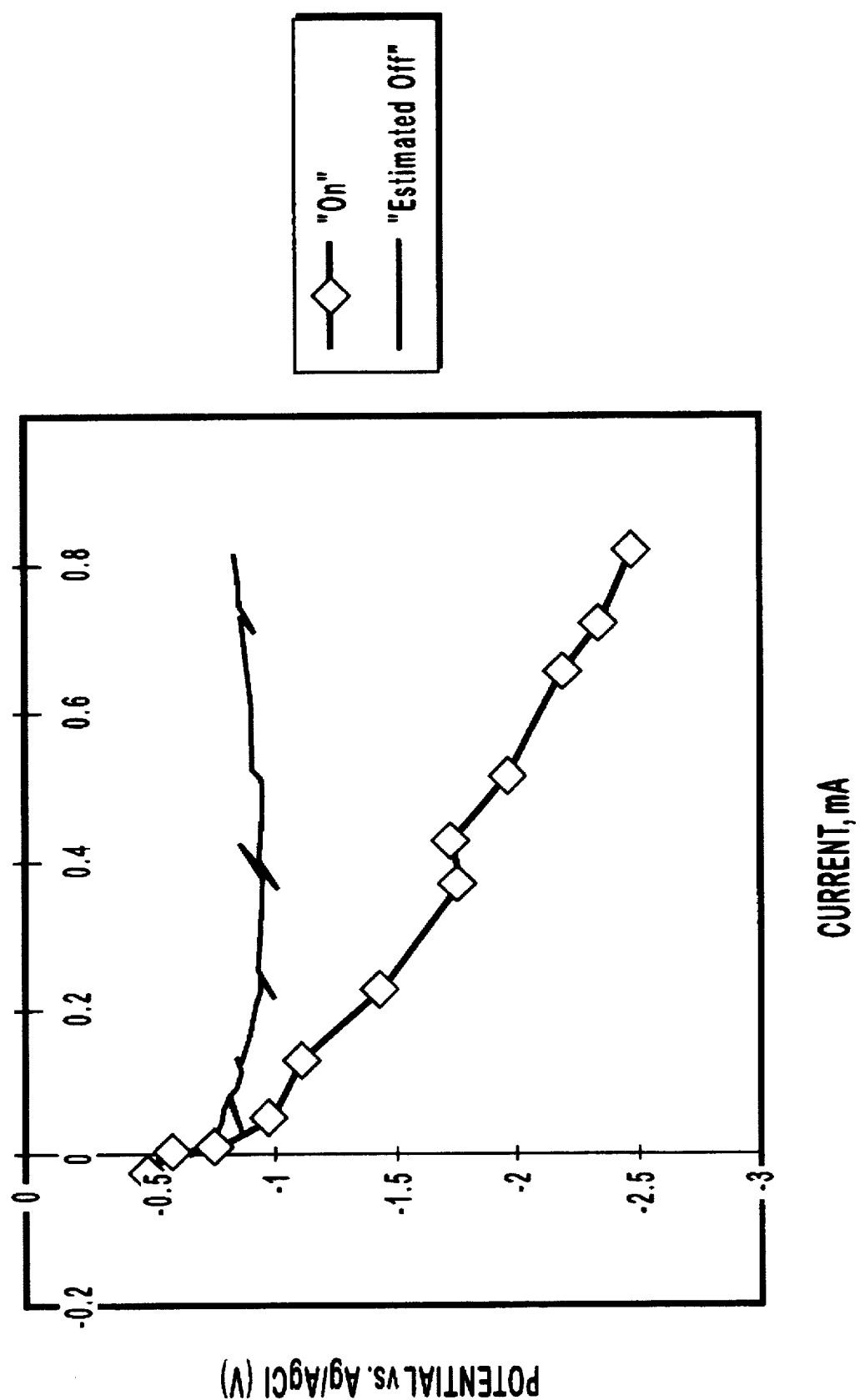
FIG. 17 is a cathodic polarization cuve measured in the field.
Figure 18:
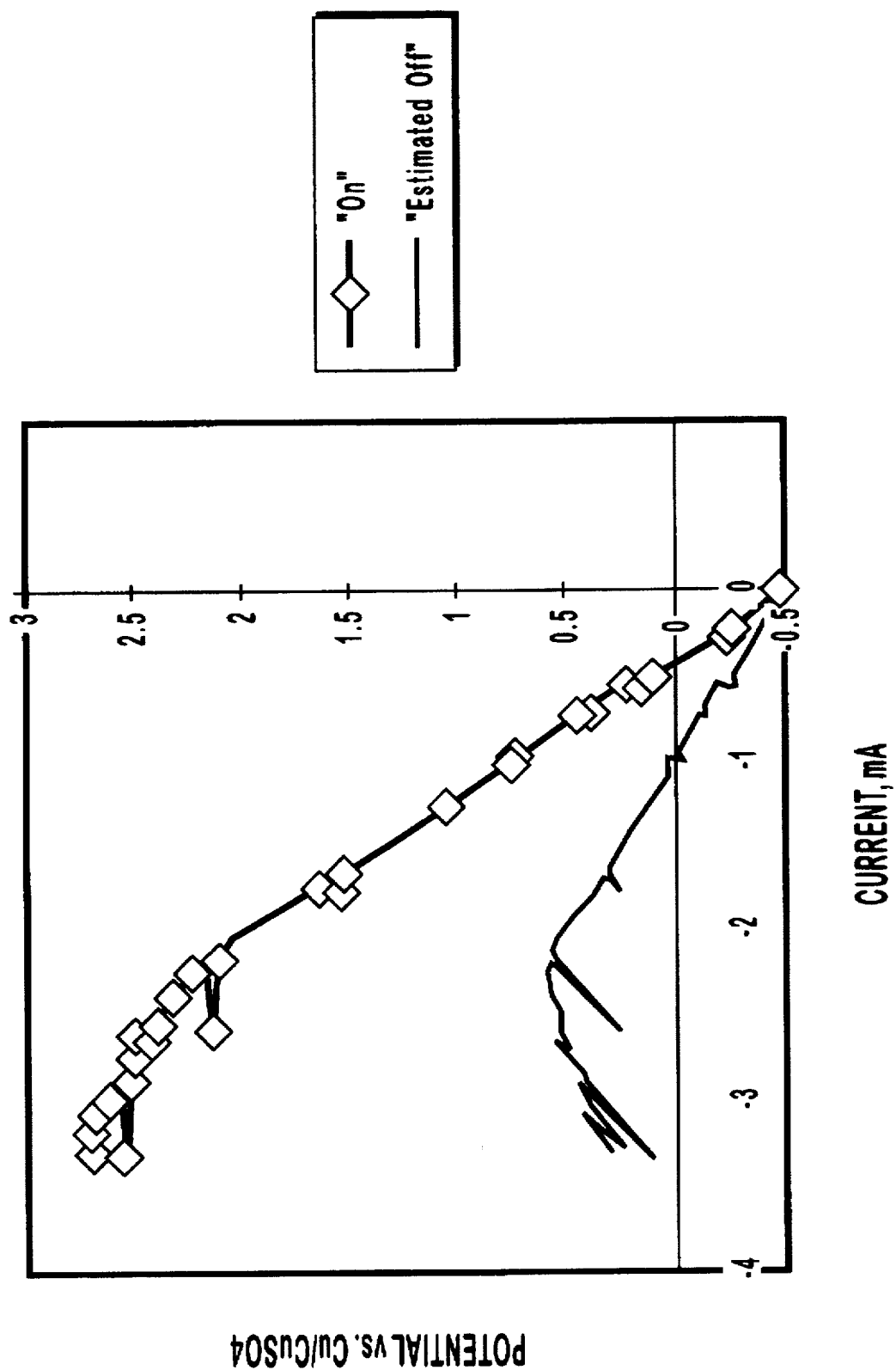
FIG. 18 is a anodic polarization cuve measured in the field.

Cathodic and anodic polarization curves were conducted at all three field sites to compare them with those obtained in the laboratory in an environment that causes SCC. Examples of the results from the polarization tests are presented in the FIGS. 17 and 18.

From the field polarization curves it was observed that Ohmic drop affects the shape of the polarization curve. No evidence of an active/passive transition were observed at any of the sites. The anodic polarization curve was consistent with that of an acidic environment.

Figure 19:
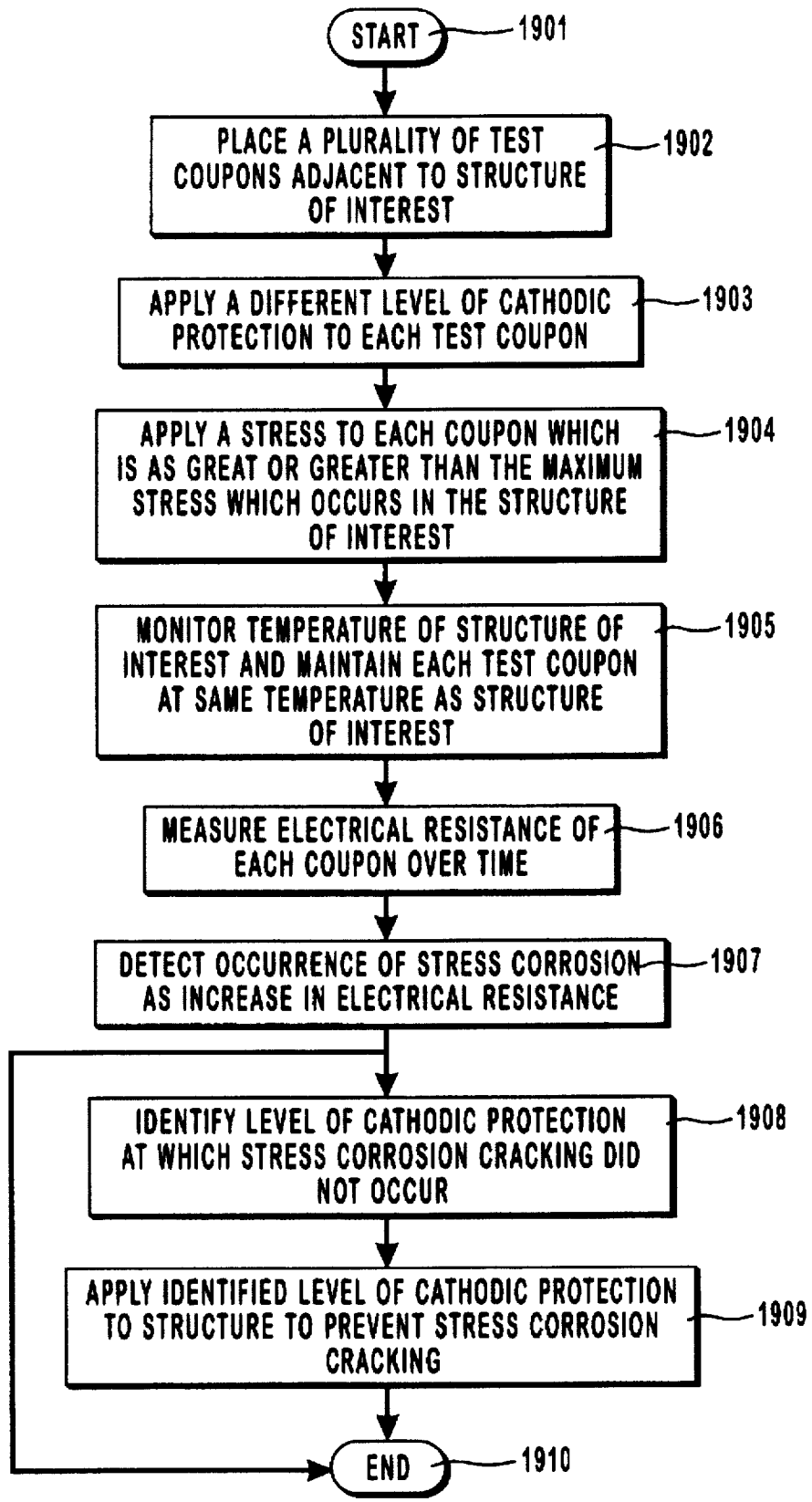
FIG. 19 is a flow diagram of the inventive method.

Examples 1 and 2 presented herein illustrate the use of the two specific embodiments of the invention in the lab and in field testing. The method of the invention is summarized in the flow diagram presented in FIG. 19. First, at step 1902, a plurality of test coupons should be placed adjacent the structure of interest, in the same environment as the structure. A different level of CP should be applied to each test coupon (step 1903); the levels of CP should be selected so as to form a range which contains the level of CP at which SCC is expected to occur. Each coupons should be subjected to a stress which is at least as great as the maximum stress to which the structure of interest is exposed (step 1904). The temperature of the structure of interest should be monitored, and the test coupons maintained at the same temperature (step 1905). Alternatively, in the case that the structure was not at its normal temperature, it would be preferable to manually set the temperature at which the test coupons were maintained. The electrical resistance of each coupon should be monitored over time (step 1906), so that SCC can be detected as an increase in coupon resistance (step 1907). If it is only desired to detect the occurrence of SCC, step 1907 is the last step of the process, and the process can be ended (step 1910). However, if is is desired to prevent SCC, the level of CP which prevented SCC in the test coupon should be identified (step 1908), and that level of CP should be applied to the structure of interest (step 1909). This should prevent the occurrance of further SCC. By following this method, the invention can be implemented in the detection and prevention of SCC in various structures and in various environments.

The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A method of detecting stress corrosion cracking in a structure, comprising the steps of:
   a) placing a plurality of test coupons adjacent to said structure;
   b) applying a different level of cathodic protection to each of said test coupons;
   c) applying a stress to each of said test coupons which is at least as great as the maximum stress which can occur in said structure;
   d) monitoring the temperature of said structure and controlling the temperature of each of said test coupons so that it matches the temperature of said structure;
   e) measuring the electrical resistance of each of said test coupons over time;
   f) detecting the occurrence of stress corrosion cracking in any of said test coupons as an increase in said electrical resistance;
   wherein the levels of cathodic protection applied to said plurality of test coupons form a range which includes the level of cathodic protection at which stress corrosion cracking is expected to occur.

2. A method in accordance with claim 1, further comprising the steps of:
   g) identifying a level of cathodic protection effective to prevent stress corrosion cracking in one of said test coupons;
   h) applying said level of cathodic protection effective to prevent stress corrosion cracking to said structure, thereby preventing stress corrosion cracking in said structure.

3. A method in accordance with claim 1, wherein said structure is a buried pipeline, and wherein said test coupons are C-rings.

4. A method in accordance with claim 1, wherein the variation in said electrical resistance of said coupons due to temperature variations is determined, and wherein the occurrence of stress corrosion cracking in any of said test coupons is detected as an as an increase in said electrical resistance which is larger than increase in said electrical resistance due to said temperature variations.

5. A system for detecting stress corrosion cracking in a structure, comprising:
   a) a plurality of test cells, each test cell comprising:
      i) a test coupon constructed of the same material as said structure and having a first end and a second end;
      ii) a temperature monitoring device for monitoring the temperature of said test coupon;
      iii) a heating element affixed to said test coupon;
      iv) an impressed current anode;
      v) a reference electrode;
      vi) a means of applying a stress to said test coupon which is at least as great as the maximum stress which can occur in said structure;
      vii) a shunt resistor having a first end and a second end, wherein the second end of said resistor is connected to the first end of said test coupon;
      viii) a current source connected to the first end of said shunt resistor and the second end of said test coupon;
      ix) a first voltage measuring device for measuring the voltage drop across said shunt resistor;
      x) a second voltage measuring device for measuring the voltage drop across said test coupon;
   b) a temperature monitoring device affixed to said structure which monitors the temperature of said structure;
   c) a temperature control system which controls each of said heating elements so that the temperature of each of said test coupons is regulated at the temperature of said structure;
   d) a plurality of potentiostat circuits, wherein each said potentiostat circuit regulates the current passing from said test coupon to said anode in one of said test cells, whereby said test coupon is held at a fixed potential with respect to said reference electrode, and wherein each of said test coupons is held a different fixed potential;
   wherein the resistance of each of said test coupons is calculated from the current provided by each said current source and said voltage drop across each said test coupon and wherein the presence of stress corrosion cracking in one of said test coupons is detected as an increase in the resistance of said test coupon.

6. A system in accordance with claim 5, wherein said structure is a buried pipeline, and wherein said test coupon is a C-ring.

7. A system in accordance with claim 5, further comprising:
   a) an impressed current anode associated with said structure;
   b) a reference electrode associated with said structure;
   c) a potentiostat circuit connected to said structure which regulates the current passing from said structure to said anode whereby said structure is held at a fixed potential with respect to said reference electrode;

wherein said structure is held at a fixed potential which was not associated with stress corrosion cracking in any of said test coupons.

8. A sensor for detecting stress corrosion cracking in buried pipelines, comprising:
   a) a three-dimensional framework constructed of a sturdy, non-conductive structural material;
   b) a plurality of C-ring coupons supported by said framework, each C-ring coupon having associated therewith:
      i) a temperature monitoring device for monitoring the temperature of test C-ring coupon;
      ii) a heating element affixed to said C-ring coupon;
      iii) an impressed current anode affixed to said framework in the vicinity of said C-ring coupon;
      iv) a reference electrode affixed to said framework in the vicinity of said C-ring coupon;
      v) a mechanism for applying a stress to said C-ring coupon.

9. A sensor in accordance with claim 8, wherein said mechanism for applying stress to said C-ring coupon comprises a threaded non-conductive rod passing through a hole in the top of said C-ring coupon and through a hole in the bottom of said C-ring coupon, fixed at the top of said C-ring coupon by two non-conductive nuts, one of said nuts being threaded onto said rod at the outer surface of said bottom of said C-ring coupon, and one of said nuts being threaded onto said rod at the inner surface of said bottom of said C-ring coupon, wherein said C-ring coupon is subjected to stress by inward movement of a third non-conductive nut which is threaded onto said rod at the outer surface of the top end of said C-ring coupon; and wherein each of said C-ring coupons has a V-notch on its outer surface, on an axis perpendicular to the axis of said threaded rod.

10. A sensor in accordance with claim 9, further comprising a compression spring positioned on said rod between said third non-conductive nut and said outer surface of said top end of said C-ring coupon.

* * * * *